(12) United States Patent
Kufe et al.

(10) Patent No.: US 6,524,832 B1
(45) Date of Patent: Feb. 25, 2003

(54) DNA DAMAGING AGENTS IN COMBINATION WITH TYROSINE KINASE INHIBITORS

(75) Inventors: Donald Kufe, Wellesley, MA (US); Ralph R. Weichselbaum, Chicago, IL (US)

(73) Assignee: Arch Development Corporation, Chicago, IL (US)

( * ) Notice: Subject to any disclaimer, the term of this patent is extended or adjusted under 35 U.S.C. 154(b) by 0 days.

(21) Appl. No.: 08/309,315

(22) Filed: Aug. 19, 1994

Related U.S. Application Data

(63) Continuation-in-part of application No. 08/192,107, filed on Feb. 4, 1994, now abandoned.

(51) Int. Cl.$^7$ .............................................. C12N 13/00
(52) U.S. Cl. ............................... 435/173.1; 435/173.4; 435/212; 424/94.5; 514/25; 514/27; 514/456; 514/457; 600/1
(58) Field of Search ........................... 435/173.1, 173.4, 435/212; 424/94.5; 514/25, 27, 456, 457; 600/1

(56) References Cited

U.S. PATENT DOCUMENTS 5,171,217 A * 12/1992 March et al. ................. 604/53
5,262,409 A * 11/1993 Margolis et al. ............ 514/183

OTHER PUBLICATIONS

Watanabe et al., Exp. Cell Res., 183, 1989, 335–342.*
Akinaga et al., Cancer Chemother., Pharmol., 1993, 32:183–189.*
Hallahan et al., Radiation Res., vol. 129, No. 3, 1992, 345–350.*
Waddick et al., Radiation Res., vol. 136, 313–319, 1993.*
Crompton et al., vol. 135, No. 3, 1993, 372–379.*
Kim et al., Br. J. Cancer, 1992, 66, 844–849.*
Saad et al., J. of Cellular Physiology, 161:142–148, 1994.*
Kharbanda et al., T. of Biol. Chem., vol. 269, No. 32, 20739–20743, 1994.*
Kharbanda et al., Oncogene, 1994, 9, 3005–3011.*
Kitamura, Y. et al., Acta Histochem. Cytochem., vol. 27(1), pp. 17–22, 1994.*
Brach et al., "Ionizing Radiation Induces Expression and Binding Activity of the Nuclear Factor $_kB$," J. Clin. Invest., 88:691–695, 1991.
Cantley et al., "Oncogenes and Signal Transduction," Cell, 64:281–302, 1991.
Datta et al., "Involvement of Reactive Oxygen Intermediates in the Induction of c–jun Gene Transcription by Ionizing Radiation," Biochemistry, 31(5):8300–8306, 1992.
Enoch and Nurse, "Mutation of the Fission Yeast Cell Cycle Control Genes Abolishes Dependence of Mitosis on DNA Replication," Cell, 60:665–673, 1990.

Gould et al., "Complementation of the Mitotic Activator, p80$^{cdc25}$, by a Human Protein–Tyrosine Phosphatase," Science, 250:1573–1576, 1990.
Hallahan et al., "Molecular Basis for the Use of Glucocorticoids, Nonsteroidals and Pentoxifylline to Minimize the Acute Effects of Radiotherapy," Cancer Research, 51:4565–4569, 1991.
Hallahan et al., "Increased tumor necrosis factor α mRNA after cellular exposure to ionizing radiation," Proc. Natl. Acad. Sci. USA, 86:10104–10107, 1989.
Hallahan et al., "Transcriptional regulation of the TNF gene by x–irradiation," Proc. Am. Assoc. Cancer Res., 31(0):75, 1990.
Hallahan et al., "Protein kinase C mediates x–ray inducibility of nuclear signal transducers EGR1 and JUN," Proc. Natl. Acad. Sci. USA, 88:2156–2160, 1991.
Hallahan et al., "Tumor Necrosis Factor Gene Expression Is Mediated by Protein Kinase C following Activation by Ionizing Radiation," Cancer Research, 51:4565–4569, 1991.
Hallahan et al., "Ketoconazole Attenuates Radiation–Induction of Tumor Necrosis Factor," J.J. Radiation Oncology, in press, 1994.
Hallahan et al., "Mechanisms of X–Ray Mediated Protooncogene c–jun Expression in Radiation–Induced Human Sarcoma Cell Lines," Int. J. Radiation Oncology Biol. Phys., 21(6):1677–1681, 1991.
Hartwell and Weinert, "Checkpoints: Controls That Ensure the Order of Cell Cycle Events," Science, 246:629–634, 1989.
Hollander and Fornace, "Induction of fos RNA by DNA–damaging Agents," Cancer Research, 49:1687–1692, 1989.
Kastan et al., "Participation of p53 Protein in the Cellular Response to DNA Damage," Cancer Research, 51:6304–6311, 1991.
Lambert and Borek, "X–ray–Induced Changes in Gene Expression in Normal and Oncogene–Transformed Rat Cell Lines," Journal of the National Cancer Institute, 80(18):1492–1497, 1988.
Mustelin and Altman, "Dephosphorylation and activation of the T cell tyrosine kinase pp56$^{1ck}$ by the leukocyte common antigen (CD45)," Oncogene, 5:809–813, 1990.
Neta et al., "Role of Interleukin 6 (IL–6) in Protection from Lethal Irradiation and in Endocrine Responses to IL–1 and Tumor Necrosis Factor," The Journal of Experimental Medicine, 175:689–694, 1992.

(List continued on next page.)

Primary Examiner—Leon B. Lankford, Jr.
(74) Attorney, Agent, or Firm—Fulbright & Jaworski

(57) ABSTRACT

The present invention relates to the signalling pathways connecting DNA damage, such as that induced by ionizing radiation or alkylating agents, and phosphorylation by tyrosine kinases.

9 Claims, 15 Drawing Sheets

OTHER PUBLICATIONS

Nurse, "Universal control mechanism regulating onset of M–phase," *Nature,* 344:503–508, 1990.

Papathanasiou et al., "Identification of an x–ray–inducible human gene and its altered expression in ataxia telangiectasia," *Proceedings of the American Association for Cancer Research,* 31:304, 1990.

Pleiman et al., "Mapping of Sites of the Src Family Protein Tyrosine Kinase $p55^{blk}$, $p59^{fyn}$, and $p56^{lyn}$ Which Interact with the Effector Molecules Phospholipase C–γ, Microtubule–Associated Protein Kinase, GTPase–Activating Protein, and Phosphatidylinositol 3–Kinase," *Molecular and Cellular Biology,* 13(9):5877–5887, 1993.

Sherman et al., "Ionizing radiation regulates expression of the c–jun protooncogene," *Proc. Natl. Acad. Sci. USA,* 87:5663–5666, 1990.

Uckun et al., "Tyrosine phosphorylation is a mandatory proximal step in radiation–induced activation of the protein kinase C signaling pathway in human B–lymphocyte precursors," *Proc. Natl. Acad. Sci. USA,* 90:252–256, 1993.

Uckun et al., "Ionizing radiation stimulates unidentified tyrosine–specific protein kinases in human B–lymphocyte precursors, triggering apoptosis and clonogenic cell death," *Proc. Natl. Acad. Sci. USA,* 89:9005–9009, 1992.

Weichselbaum et al., "Radiation–resistant and repair–proficient human tumor cells may be associated with radiotherapy failure in head– and neck–cancer patients," *Proc. Natl. Acad. Sci. USA,* 83:2684–2688, 1986.

Weichselbaum et al., "X–Ray Sensitivity of Fifty–three Human Diploid Fibroblast Cell Strains from Patients with Characterized Genetic Disorders," *Cancer Research,* 40:902–925, 1980.

Yamanashi et al., "Activation of Src–like protein–tyrosine kinase Lyn and its association with phosphatidylinositol 3–kinase upon C–cell antigen receptor–mediated signaling," *Proc. Natl. Acad. Sci. USA,* 89:1118–1122, 1992.

Abou–Shoer et al., Flavonoids from *Koelreuteria Henryi* And Other Sources As Protein–Tyrosine Kinase Inhibitors, *J. Nat. Proc.,* 56(6):967–9, 1993.

Atherton–Fessler et al., "Mechanisms of $p34^{cdc2}$ Regulation," *Molecular and Cellular Biology,* 13(3):1675–1685, 1993.

Al–Khodiary and Carr, DNA repair mutants defining $G_2$ checkpoint pathways in *Schizosaccharomyces pombe, The EMBO Journal,* 11(4):1343–1350, 1992.

Barbet and Carr, "Fission yeast wee1 protein kinase is not required for DNA damage–dependent mitotic arrest," *Nature,* 364:824–827, 1993.

Bhuyan et al., "Lethality, DNA Alkylation and Cell Cycle Effects of Adozelesin (U–73975) on Rodent and Human Cells," *Cancer Research,* 52:5687–5692, 1992.

Bonni et al., "Characterization of a Pathway for Ciliary Neurotrophic Factor Signaling to the Nucleus," *Science,* 262:1575–1579, 1993.

Buchdunger et al., "4,5–Dianilinophthalimide: A protein–tyrosine kinase inhibitor with selectivity for the epidermal growth factor receptor signal transduction pathway and potent in vivo antitumor activity," *Proc. natl. Acad. Sci. USA,* 91:2334–2338, 1994.

Carter et al., "Tyrosine phosphorylation of phospholipase C induced by membrane immunoglobulin in B lymphocytes," *Proc. Natl. Acad. Sci. USA,* 88:2745–2749, 1991.

Casillas et al., "Stimulation of B–cells via the Membrane Immunoglobulin Receptor or with Phorbol Myristate 13–Acetate Induces Tyrosine Phosphorylation and Activation of a 42–kDa Microtubule–associated Protein–2 Kinase," *The Journal of Biological Chemistry,* 266(28):19088–19094, 1991.

Chan et al., "Selective inhibition of the growth of ras–transformed human bronchial epithelial cells by emodin, a protein–tyrosine kinase inhibitor," *Biochemical and Biophysical Research Communications,* 193(3):1152–1158, 1993.

Chen et al., "Structure of malhamensilipin A, an inhibitor of protein tyrosine kinase, from the cultured chrysophyte *poterioochromonas malhamensis,"* *Journal of Natural Products,* 57(4):524–527, 1994.

Datta et al., "Ionizing radiation activates transcription of the EGR1 gene via CArG elements," *Proc. Natl. Acad. Sci. USA,* 80:10149–10153, 1992.

Datta et al., "Reactive oxygen intermediates target $CC(A/T)_6GG$ sequences to mediate activation of the early growth response 1 transcription factor gene by ionizing radiation," *Proc. Natl. Acad. Sci. USA,* 90:2419–2422, 1993.

Desai et al., "Activation of Human Cyclin–Dependent Kinase In Vitro," *Molecular Biology of the Cell,* 3:571–582, 1992.

Devary et al., "The Mammalian Ultraviolet Response is Triggered by Activation of the Src Tyrosine Kinases," *Cell,* 71:1081–1091, 1992.

Gillespie et al., "Inhibition of pancreatic cancer cell growth in vitro by the tyrphostin group of tyrosine kinase inhibitors," *Br. J. Cancer,* 68:1122–1126, 1993.

Gold et al., "Membrane Ig Cross–Linking Regulates Phosphatidylinositol 3–Kinase In B Lymphocytes," *The Journal of Immunology,* 148(7):2012–2122, 1992.

Hartley et al., "DNA sequence selectivity of guanine–N7 alkylation by nitrogen mustards is preserved in intact cells," *Nucleic Acids Research,* 20(12):3175–3178, 1992.

Hempel et al., "Tyrosine Phosphorylation of Phospholipase C–$\lambda_2$ upon Cross–linking of Membrane Ig on Murine B Lymphocytes," *The Journal of Immunology,* 148(10):3021–3027, 1992.

Jayasuriya et al., "Emodin, A Protein Tyrosine Kinase Inhibitor From *Polygonum Cuspidatum,"* *J. Nat. Proc.,* 55(5):696–8, 1992.

Hsu et al., "Inhibition Kinetics and Selectivity of the Tyrosine Kinase Inhibitor Erbstatin and a Pyridone–Based Analogue," *Biochemical Pharmacology,* 43(11):2471–2477, 1992.

Kakeya et al., "Isolation of a novel substrate–competitive tyrosine kinase inhibitor, desmal, from the plant *Desmos chinensis,"* *FEBS,* 320(2):169–172, 1993.

Khetarpal et al., "Dispositional characteristics of a tyrosine kinase inhibitor (RG 14620) in rats and rabbits following intravenous administration or dermal application," *Drug Metabolism and Disposition,* 22(2):216–223, 1994.

Larner et al., "Tyrosine Phosphorylation of DNA Binding Proteins by Multiple Cytokines," *Science,* 261:1730–1733, 1993.

Merkel, et al., "Inhibition of EGF—Induced Vasoconstriction in Isolated Rabbit Aortic Rings with the Tyrosine Kinase Inhibitor RG50864," *Biochemical and Biophysical Research Communications,*192(3):1319–1326, 1993.

Nakamura et al., "Redox regulation of a src family protein tyrosine kinase $p56^{1ck}$ in T cells," *Oncogene,* 8:3133–3139, 1993.

O'Connor et al., "Relationships between cdc2 Kinase, DNA Cross–linking, and Cell Cycle Perturbations Induced by Nitrogen Mustard," *Cell Growth & Differ.,* 3:43–52, 1992.

Ohmichi et al., "The Tyrosine Kinase Inhibitor Tyrphostin Blocks the Cellular Actions of Nerve Growth Factor," *Biochemistry,* 32:4650–4658, 1993.

Okabe et al., "BE–23372M, A Novel Protein Tyrosine Kinase Inhibitor I. Producing Organism, Fermentation, Isolation and Biological Activities," *The Journal of Antibiotics,* 47(3):289–293, 1994.

Parker et al., "p107$^{wee1}$ is a dual–specificity kinase that phosphorylates p34$^{cdc2}$ on tyrosine 15," *Proc. Natl. Acad. Sci. USA,* 89:2917–2921, 1992.

Rauth et al., "The nucleotide and partial amino acid sequences of rat fetuin," *Eur. J. Biochem.,* 204:523–529, 1992.

Rewcastle et al., "Tyrosine Kinase Inhibitors. 3. Structure–Activity Relationships for Inhibition of Protein Tyrosine Kinases by Nuclear–Substituted Derivatives of 2,2'–Dithiobis (1–methyl–N–phenyl–1H–indole–3–carboxamide)," *J. Med. Chem.,* 37:2033–2042, 1994.

Rowley et al., "Checkpoint controls in *Schizosaccharomyces pombe:* rad1," *The EMBO Journal,* 11(4):1335–1342, 1992.

Ruff–Jamison et al., "Induction by EGF and Interferon–λ of Tyrosine Phosphorylated DNA Binding Proteins in Mouse Liver Nuclei," *Science,* 261:1733–1736, 1993.

Smyth et al., "Non–Amine Based Analogues of Lavendustin A as a Protein–Tyrosine Kinase Inhibitors," *J. Med. Chem.,* 36:3010–3014, 1993.

Smyth et al., "Hydroxylated 2–(5'–Salicyl)naphthalenes as Protein–Tyrosine Kinase Inhibitors," *J. Med. Chem.,* 36:3015–3020, 1993.

Solomon et al., "Role of Phosphorylation in p37$^{cdc2}$ Activation: Identification of an Activating Kinase," *Molecular Biology of the Cell,* 3:13–27, 1992.

Sugata et al., "Inhibition of Serum–Induced M–Phase Progression by a Tyrosine Kinase Inhibitor, Erbstatin," *Biochemical and Biophysical Communications,* 194(1):239–245, 1993.

Tanaka et al., "BE–23372M, A Novel Protein Tyrosine Kinase Inhibitor III. Synthesis," *Antibiot. (Tokyo),* 47(3):297–300, 1994b.

Tanaka et al., "BE23372M, A Novel Protein Tyrosine Kinase Inhibitor II. Physico–Chemical Properties and Structure Elucidation," *The Journal of Antibiotics,* 47(3):294–296, 1994.

Thakkar et al., "Synthesis and Protein–Tyrosine Kinase Inhibitory Activity of Polyhydroxylated Stilbene Analogues of Piceatannol," *J. Med. Chem.,* 36:2950–2955, 1993.

Yoneda et al., "The Antiproliferative Effects of Tyrosine Kinase Inhibitors Tyrphostins on a Human Squamous Cell Carcinoma in Vitro and in Nude Mice," *Cancer Research,* 51:4430–4435, 1991.

Sherman et al., "Ionizing radidation regulates expression of the c–jun proto–oncogene," *Proc. Am. Assoc. Cancer Res.,* 31(0):13, 1990.

"Cell Differentiation Inducer Contains a DNA Synthesis Inhibitor and Specified Tyrosine Kinase Inhibitor," *Derwent Publ. Ltd.,* 9201: Apr. 1990; "Cell Differentiation Inducer," *Patent Abstracts of Japan,* 14(310):C0736, Apr. 1990.

Ødǫm, et al., "Signal Transduction by HLA Class II Molecules in Human T Cells: Induction of LFA–1–Dependent and Independent Adhesion," *Human Immunol,* 35(2):71–84, Oct. 1992.

Hallahan, et al., "X–Ray Induced Protein Kinase C Activation Mediates Proto–Oncogene Jun Expression (Meeting Abstract)," *Database Cancerlit,* 830416(159):S9, Apr. 1991; "Workshop on Neoplastic Transformation In Human Cell Systems In Vitro: Mechanisms of Carcinogeneses," p. S9, Apr. 1991.

Darzynkiewicz, et al., "Apoptotic Mechanism Of Cell Death During Treatment of Acute Leukemias (Meeting Abstract)," *Database Cancerlit,* 1126890(159):164, Jul. 1993; "Molecular Biology of Hematopoiesis—8th Symposium," p. 164, 1993.

Uckun, et al., "Ionizing Radiation Stimulates Unidentified Tyrosine—Specific Protein Kinases In Human B–Lymphocyte Precursors, Triggering Apoptosis and Clonogenic Cell Death," *Proc. Natl. Acad. Sci. USA,* 89(19):9005–9009, Oct., 1992.

\* cited by examiner

SEQUENCE LISTING (1) GENERAL INFORMATION:

(iii) NUMBER OF SEQUENCES: 2

(2) INFORMATION FOR SEQ ID NO:1:

```
        (i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:1:

Ile Glu Lys Ile Gly Glu Gly Thr Tyr Gly Val Val Tyr Lys
1               5                   10

(2) INFORMATION FOR SEQ ID NO:2:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:2:

Ile Glu Lys Ile Gly Glu Gly Thr Phe Gly Val Val Tyr Lys
1               5                   10
```

DNA DAMAGING AGENTS IN COMBINATION WITH TYROSINE KINASE INHIBITORS

The present application is a continuation-in-part of U.S. patent application Ser. No. 08/192,107, filed Feb. 4, 1994, now abandoned. The entire text of which disclosure is specifically incorporated herein by reference without disclaimer.

The U.S. Government owns rights in the present invention pursuant to grant number CA19589 from the National Cancer Institute.

BACKGROUND OF THE INVENTION

1. Field of the Invention

The present invention relates generally to the field of biochemical pathways. More particularly, it concerns the pathways connecting DNA damage and phosphorylation by tyrosine kinases.

2. Description of the Related Art

Current treatment methods for cancer, including radiation therapy alone, surgery and chemotherapy, are known to have limited effectiveness. Cancer mortality rates will therefore remain high well into the 21st century. The rational development of new cancer treatment methods will depend on an understanding of the biology of the cancer cell at the molecular level.

Certain cancer treatment methods, including radiation therapy, involve damaging the DNA of the cancer cell. The cellular response to DNA damage includes activation of DNA repair, cell cycle arrest and lethality (Hall, 1988). The signaling events responsible for the regulation of these events, however, remain unclear.

Several checkpoints in cell cycle progression control growth in response to diverse positive and negative regulatory signals (Lau & Pardee, 1982). Ionizing radiation, for example, slows growth by inducing delays in $G_1/S$ and $G_2$ phases of the cell cycle. The available evidence suggests that $G_2$ arrest in necessary for repair of DNA damage before entry into mitosis (Steinman et al., 1991; Weinert & Hartwell, 1988). Genetic studies in Saccharomyces cerevisiae have demonstrated that the RAD9 protein controls $G_2$ arrest induced by DNA damage (Schiestl et al., 1989; Murray, 1989). Mutants of the rad9 locus are unable to delay entry into mitosis following exposure to genotoxic agents and thereby replicate damaged DNA. Although the mammalian homolog of rad9 remains unidentified, other studies in various eukaryotic cells have demonstrated that entry into mitosis is regulated by a 34 kD serine/threonine protein kinase, designated $p34^{cdc2}$ (Nurse, 1990; Pines & Hunter, 1989; Russell & Nurse, 1987).

Recent studies have shown that exposure of eukaryotic cells to ionizing radiation is associated with induction of certain early response genes that code for transcription factors. Members of the jun/fos and early growth response (EGR) gene families are activated by ionizing radiation (Sherman et al., 1990; Datta et al., 1992a). Expression and DNA binding of the nuclear factor kB (NF-kB) are also induced in irradiated cells (Brach et al., 1991; Uckun et al., 1992a). Other studies have shown that levels of the tumor suppressor p53 protein increase during X-ray-induced arrest of cells in Gi phase (Kastan et al., 1991; 1992). The activation of these transcription factors presumably represents transduction of early nuclear signals to longer term changes in gene expression that constitute the response to irradiation. Ionizing radiation also induces protein kinase C (PKC) and protein tyrosine kinase activities (Hallahan et al., 1990; Uckun et al., 1993). However, the specific kinases responsible for these activities and their substrates require further study.

Mitomycin C (MMC) is an antitumor antibiotic isolated from Streptomyces caespitosus that covalently binds to DNA (Tomasz et al., 1988). This agent induces both monofunctional and bifunctional DNA lesions (Carrano et al., 1979). Other studies have demonstrated that MMC stimulates the formation of hydroxyl radicals (Dusre et al., 1989). Although the precise mechanism of action of this agent is unclear, MMC-induced cytotoxicity has been attributed to DNA alkylation and the formation of interstrand cross-links (Carrano et al., 1979; Dusre et al., 1989; Tomasz et al., 1988). Treatment of mammalian cells with MMC is associated with inhibition of DNA synthesis and induction of sister-chromatid exchange (Carrano et al., 1979). Previous work has demonstrated that MMC also enhances transcription of HIV-1 and collagenase promoter constructs transfected into HeLa cells (Stein et al., 1989). These studies indicated that AP-1 is involved in MMC-induced activation of the collagenase enhancer. However, little is known about the effects of this agent on other signaling events.

Protein tyrosine phosphorylation contributes to the regulation of cell growth and differentiation. Protein tyrosine kinases can be divided into receptor-type and nonreceptor-type (Src-like) kinases (Cantley et al., 1991; Hanks et al., 1988; Bonni et al., 1993; Larner et al., 1993; Ruff-Jamison et al., 1993). Several protein tyrosine kinases have been purified from the cytosolic fractions of various tissues (Nakamura et al., 1988; Wong & Goldberg, 1984; Zioncheck et al., 1986).

The Src-like kinases, which can associate with receptors at the plasma membrane, induce rapid tyrosine phosphorylation and/or activation of effectors such as phospholipase C-γ1 (PLCγ1) (Carter et al., 1991), PLCγ2 (Hempel et al., 1992), mitogen-activated protein (MAP) kinase (Casillas et al., 1991), GTPase activating protein (GAP) (Gold et al., 1992a) and phosphati-dylinositol 3-kinase (PI3-K) (Gold et al., 1992b). Recent studies have demonstrated an increase in tyrosine phosphorylation following irradiation of B-lymphocyte precursors (Uckun et al., 1993). Studies of $p59^{fyn}$, $p56/p53^{lyn}$, $p55^{blk}$ and $p56^{lck}$ activity demonstrated that these Src-family tyrosine kinases were not responsible for radiation-induced tyrosine phosphorylation (Uckun et al., 1992a). These findings suggested that other protein tyrosine kinases, perhaps of the receptor-type, are involved in the response of cells to ionizing radiation.

Varying the environmental conditions following exposure to ionizing radiation or DNA damaging agents can influence the proportion of cells that survive a given dose due to the expression or repair of potentially lethal damage (PLD). The damage is potentially lethal because while under normal circumstances it causes cell death, manipulation of the post-irradiation environment can modify the cell response. Studies show that cell survival can be increased if the cells are arrested in the cell cycle for a protracted period of time following radiation exposure, allowing repair of DNA damage. (Hall, 1988). Thus, PLD is repaired and the fraction of cells surviving a given dose of x-rays is increased if conditions are suboptimal for growth, such that cells do not have to undergo mitosis while their chromosomes are damaged.

For some diseases, e.g., cancer, ionizing radiation is useful as a therapy. Methods to enhance the effects of radiation, thereby reducing the necessary dose, would greatly benefit cancer patients. Therefore, methods and compositions were sought to enhance radiation effects by increasing the sensitivity of cells to damage from ionizing radiation and DNA damaging agents such as alkylating compounds. Cells that are irradiated or treated with DNA damaging agents halt in the cell cycle at $G_2$, so that an inventory of chromosome damage can be taken and repair initiated and completed before mitosis is initiated. By blocking the stress or survival response in these cells, they undergo mitosis with damaged DNA, express the mutations, and are at a greater risk of dying.

SUMMARY OF THE INVENTION

In one aspect, the present invention provides a process of selectively activating the lyn family of Src-like tyrosine kinases in a cell that expresses the lyn gene. In accordance with that process, the cell is exposed to an effective activating dose of ionizing radiation. In a preferred embodiment, $p56/p53^{lyn}$ is activated.

In another aspect, the present invention provides a process of stimulating tyrosine phosphorylation of Src-like tyrosine kinase substrates. In such a process, a cell that expresses the lyn gene is exposed to an effective activating dose of ionizing radiation. Exemplary Src-like tyrosine kinase substrates include phospholipase C-γ1, phospholipase C-γ2, mitogen-activated protein kinase, GTPase activating protein, phosphatidylinositol 3-kinase and enolase.

In another aspect, the present invention provides a process of inhibiting ionizing radiation induced tyrosine phosphorylation in a cell that expresses the lyn gene comprising inhibiting the activity of $p56/p53^{lyn}$. In a preferred embodiment, $p56/p53^{lyn}$ activity is inhibited by exposing the cell to an effective inhibitory amount of herbimycin A or genistein.

The present invention also provides a process of stimulating the activity of $p56/p53^{lyn}$ with out the concomitant stimulation of other Src-like tyrosine kinases by treating cells with genotoxic alkylating agents. In such a process, a cell that expresses the lyn gene is exposed to an effective activating dose of an alkylating agent, for example, mitomycin C. Subsequent to this exposure, the cells are treated with a tyrosine kinase inhibitor that inhibits the activity of $p56/p53^{lyn}$, preventing phosphorylation on $p34^{cdc2}$ on tyrosine, effectively allowing the cells to progress past $G_2$ arrest.

The $G_2$ phase is the point in the cell cycle used DNA repair following damage from ionizing radiation or alkylating agents. Other DNA damaging agents also are able to cause cell arrest in the $G_2$ phase. By preventing delays in $G_2$ cells will enter mitosis before the DNA is repaired and therefore the daughter cells will likely die. By lengthening the $G_2$ period, cells undergo repair and survival following exposure to a DNA damaging agent increases.

DNA damaging agents or factors are defined herein as any chemical compound or treatment method that induces DNA damage when applied to a cell. Such agents and factors include ionizing radiation and waves that induce DNA damage, such as, γ-irradiation, X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., alkylating agents such as mitomycin C, adozelesin, cis-platinum, and nitrogen mustard. The invention also encompasses the use of a combination of one or more DNA damaging agents, whether ionizing radiation-based or actual compounds, with one or more tyrosine kinase inhibitors.

To kill a cell in accordance with the present invention, one would generally contact the cell with a DNA damaging agent and a tyrosine kinase inhibitor in a combined amount effective to kill the cell. The term "in a combined amount effective to kill the cell" means that the amount of the DNA damaging agent and inhibitor are sufficient so that, when combined within the cell, cell death is induced. Although not required in all embodiments, the combined effective amount of the two agents will preferably be an amount that induces more cell death than the use of either element alone, and even one that induces synergistic cell death in comparison to the effects observed using either agent alone. A number of in vitro parameters may be used to determine the effect produced by the compositions and methods of the present invention. These parameters include, for example, the observation of net cell numbers before and after exposure to the compositions described herein.

Similarly, a "therapeutically effective amount" is an amount of a DNA damaging agent and tyrosine kinase inhibitor that, when administered to an animal in combination, is effective to kill cells within the animal. This is particularly evidenced by the killing of cancer cells within an animal or human subject that has a tumor. "Therapeutically effective combinations" are thus generally combined amounts of DNA damaging agents and tyrosine kinase inhibitors that function to kill more cells than either element alone and that reduce the tumor burden.

The present invention generally provides novel strategies for the improvement of chemotherapeutic intervention. It is proposed that the combination of a DNA damaging agent and a tyrosine kinase inhibitor will lead to synergistic cancer cell killing effects over and above the actions of the individual DNA damaging component.

In certain embodiments, a process of enhancing cell death is provided, which comprises the steps of first treating cells or tumor tissue with a DNA damaging agent, such as ionizing radiation or an alkylating agent, followed by contacting the cells or tumors with a protein kinase inhibitor, preferably a tyrosine kinase inhibitor. Examples of alkylating agents are mitomycin C, adozelesin, nitrogen mustard, cis-platinum. Exemplary tyrosine kinase inhibitors are genistein or herbimycin.

DNA damaging agents or factors are defined herein as any chemical compound or treatment method that induces DNA damage when applied to a cell. Such agents and factors include radiation and waves that induce DNA damage, such as, γ-irradiation, X-rays, UV-irradiation, microwaves, electronic emissions, and the like. A variety of chemical compounds, which may be described as "chemotherapeutic agents", also function to induce DNA damage, all of which are intended to be of use in the combined treatment methods disclosed herein. Chemotherapeutic agents contemplated to be of use, include, e.g., mitomycin C (MMC), adozelesin, cis-platinum, nitrogen mustard, 5-fluorouracil (5FU), etoposide (VP-16), camptothecin, actinomycin-D, cisplatin (CDDP).

The invention provides, in certain embodiments, methods and compositions for killing a cell or cells, such as a malignant cell or cells, by contacting or exposing a cell or population of cells to one or more DNA damaging agents and one or more tyrosine kinase inhibitors in a combined amount effective to kill the cell(s). Cells that may be killed using the invention include, e.g., undesirable but benign cells, such as benign prostate hyperplasia cells or over-active thyroid cells; cells relating to autoimmune diseases, such as B cells that produce antibodies involved in arthritis, lupus, myasthenia gravis, squamous metaplasia, dysplasia and the like. Although generally applicable to killing all undesirable cells, the invention has a particular utility in killing malignant cells. "Malignant cells" are defined as cells that have lost the ability to control the cell division cycle, as leads to a "transformed" or "cancerous" phenotype.

To kill cells, such as malignant cells, using the methods and compositions of the present invention, one would generally contact a "target" cell with at least one DNA damaging agent and at least one tyrosine kinase inhibitor in a combined amount effective to kill the cell. This process may involve contacting the cells with the DNA damaging agent (s) or factor(s) and the tyrosine kinase inhibitor at the same time. This may be achieved by contacting the cell with a single composition or pharmacological formulation that includes both agents, or by contacting the cell with two distinct compositions or formulations, at the same time, wherein one composition includes the DNA damaging agent and the other composition includes the tyrosine kinase inhibitor.

Naturally, it is also envisioned that the target cell may be first exposed to the DNA damaging agent(s) and then contacted with a tyrosine kinase inhibitor, or vice versa. In such embodiments, one would generally ensure that sufficient time elapses, so that the two agents would still be able to exert an advantageously combined effect on the cell. In such instances, it is contemplated that one would contact the cell with both agents within about 12 hours of each other, and more preferably within about 6 hours of each other, with a delay time of only about 4 hours being most preferred. These times are readily ascertained by the skilled artisan.

The terms "contacted" and "exposed", when applied to a cell, are used herein to describe the process by which a tyrosine kinase inhibitor, such as genistein or herbimycin A, and a DNA damaging agent or factor are delivered to a target cell or are placed in direct juxtaposition with the target cell. To achieve cell killing, both agents are delivered to a cell in a combined amount effective to kill the cell, i.e., to induce programmed cell death or apoptosis. The terms, "killing", "programmed cell death" and "apoptosis" are used interchangeably in the present text to describe a series of intracellular events that lead to target cell death.

Tyrosine kinases participate in diverse signalling pathways, and also participate in signal transduction in smooth muscle. "Genistein", as used herein, refers to the compound described in the Merck Index (7th Edition, 1960, p 474), or a derivative or analogue thereof that functions as a tyrosine kinase inhibitor. The ability of a genistein analogue to inhibit a tyrosine kinase, may be readily determined by methods known to those of skill in the art, as described, for example in Akiyama et al. (1987), incorporated herein by reference. Also encompassed are genistein-like compounds that form an active tyrosine kinase inhibitor upon ingestion.

The present invention also provides advantageous methods for treating cancer that, generally, comprise administering to an animal or human patient with cancer a therapeutically effective combination of a DNA damaging agent and a tyrosine kinase inhibitor. Chemical DNA damaging agents and/or inhibitors may be administered to the animal, often in close contact to the tumor, in the form of a pharmaceutically acceptable composition. Direct intralesional injection is contemplated, as are other parenteral routes of administration, such as intravenous, percutaneous, endoscopic, or subcutaneous injection.

In terms of contact with a DNA damaging agent, this may be achieved by irradiating the localized tumor site with ionizing radiation such as X-rays, UV-light, γ-rays or even microwaves. Alternatively, the tumor cells may be contacted with the DNA damaging agent by administering to the animal a therapeutically effective amount of a pharmaceutical composition comprising a DNA damaging compound, such as mitomycin C, adozelesin, cis-platinum, and nitrogen mustard. A chemical DNA damaging agent may be prepared and used as a combined therapeutic composition, or kit, by combining it with a tyrosine kinase inhibitor, as described above.

Other embodiments of the invention concern compositions, including pharmaceutical formulations, comprising a DNA damaging agent in combination with a tyrosine kinase inhibitor. These compositions may be formulated for in vivo administration by dispersion in a pharmacologically acceptable solution or buffer. Suitable pharmacologically acceptable solutions include neutral saline solutions buffered with phosphate, lactate, Tris, and the like. Preferred pharmaceutical compositions of the invention are those that include, within a pharmacologically acceptable solution or buffer, mitomycin C in combination with genistein or herbimycin A.

Still further embodiments of the present invention are kits for use in killing cells, such as malignant cells, as may be formulated into therapeutic kits for use in cancer treatment. The kits of the invention will generally comprise, in suitable container means, a pharmaceutical formulation of a DNA damaging agent and a pharmaceutical formulation of a tyrosine kinase inhibitor. These agents may be present within a single container, or these components may be provided in distinct or separate container means.

The components of the kit are preferably provided as a liquid solution, or as a dried powder. When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

Although kits have been described as part of this invention, it should be noted that the use of ionizing radiation to create DNA damage is an important aspect of the invention not specifically provided in kit form.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 2A, HL-60 cells were exposed to the indicated concentrations of MMC for 1 h. In FIG. 2B, cells were exposed to $10^{-5}$ M MMC for the indicated times. Anti-Lyn immunoprecipitates were incubated with [$\gamma$-$^{32}$p] ATP and enolase. Phosphorylated protein was analyzed by SDS-PAGE and autoradiography. In FIG. 2C, anti-Lyn immunoprecipitates were analyzed by immunoblotting with anti-Lyn.

In FIG. 4A, cells were treated with $10^{-5}$ M herbimycin A (H) or genistein (G) for 1 h and then MMC for an additional 1 h. In FIG. 4B, cells were treated with $5 \times 10^{-5}$ M H7 for 1 h and then MMC for 1 h. Anti-Lyn immunoprecipitates were analyzed for phosphorylation of p56/p53$^{lyn}$ and enolase. In FIG. 4C, cells were treated with MMC for 1 h. Anti-Lyn immunoprecipitates were analyzed for phosphorylation of p56/p53$^{lyn}$ and enolase. Lysates from untreated HL-60 cells were immunoprecipitated with anti-Lyn. MMC ($10^{-5}$ M) was added to the kinase reaction and incubated for 15 min. The reaction was analyzed for phosphorylation of p56/p53$^{lyn}$ and enolase.

In FIG. 6A, cell lysates were incubated with GST or GST-Lyn proteins immobilized on beads. The resulting complexes were separated by SDS-PAGE and analyzed by immunoblotting with anti-cdc2 antibody. In FIG. 6B, lysates from control (labeled HL-60) and MMC-treated cells were subjected to immunoprecipitation with anti-cdc2. The immune complexes were assayed for in vitro kinase activity by incubation with [$\gamma$-$^{32}$P]ATP. One aliquot of the kinase reaction was analyzed by SDS-PAGE and autoradiography. The other aliquot was washed to remove free ATP and boiled in SDS buffer to disrupt complexes. A secondary immunoprecipitation was then performed with anti-Lyn. The anti-Lyn immunoprecipitates were separated by SDS-PAGE and analyzed by autoradiography.

In FIG. 7A, cell lysates were subjected to immunoprecipitation with anti-cdc2. The immunoprecipitates were analyzed by SDS-PAGE and immunoblotting with anti-P-Tyr. In FIG. 7B, cell lysates were subjected to immunoprecipitation with anti-cdc2 and immunoblot analysis with anti-cdc2.

In FIG. 9A, Cell lysates were subjected to immunoprecipitation with anti-Fyn antibodies; in FIG. 9B, cell lysates were subjected to immunoprecipitation with anti-Lyn antibodies; and in FIG. 9C, cell lysates were subjected to immunoprecipitation with anti-Lck antibodies. Autophosphorylation reactions were performed by adding [$\gamma$-$^{32}$P]ATP for 10 min at 30° C. Phosphorylated protein was analyzed by 10% SDS-PAGE and autoradiography.

In FIG. 10A, the immunoprecipitates were analyzed in autophosphorylation reactions. In FIG. 10B, enolase phosphorylation assays are shown. Samples were separated in 10% SDS-PAGE gels and analyzed by autoradiography. The fold increase of Enolase phosphorylation, increased as measured by scintillation counting of the excised bands, is indicated at the bottom.

In FIG. 12A, HL-60 cells were either treated with $H_2O_2$ for the indicated times or pretreated with 30 mM NAC for 1 h, irradiated (200 cGy) and harvested at 12 h. In FIG. 12B, HL-60 cells were treated with 10 $\mu$M herbimycin (H) or 10 $\mu$M genistein (G) for 1 h, irradiated (200 cGy) and then harvested at 12 h. Cell lysates were immunoprecipitated with anti-Lyn and the immunoprecipitates were analyzed for phosphorylation of p56/p53$^{lyn}$ and enolase.

In FIG. 13A, soluble proteins were subjected to immunoblot (IB) analysis with anti-P-Tyr; and in FIG. 13B soluble proteins were subjected to immunoblot (IB) analysis with anti-p34$^{cdc2}$ antibodies. The arrow indicates the position of 34 kD signals.

In FIG. 14A, soluble proteins were subjected to immunoblot (IB) analysis with anti-P-Tyr; and in FIG. 14B, soluble proteins were subjected to immunoblot (IB) analysis with anti-p34$^{cdc2}$ antibodies. The arrows indicate the position of the 34 kD signals.

In FIG. 15A, the immunoprecipitates were subjected to immunoblot (IB) analysis with anti-P-Tyr antibodies; and in FIG. 15B, the immunoprecipitates were subjected to immunoblot (IB) analysis with anti-p34$^{cdc2}$ antibodies.

DETAILED DESCRIPTION OF THE PREFERRED EMBODIMENTS

Figures 1A, 1B, 1C, 1D:
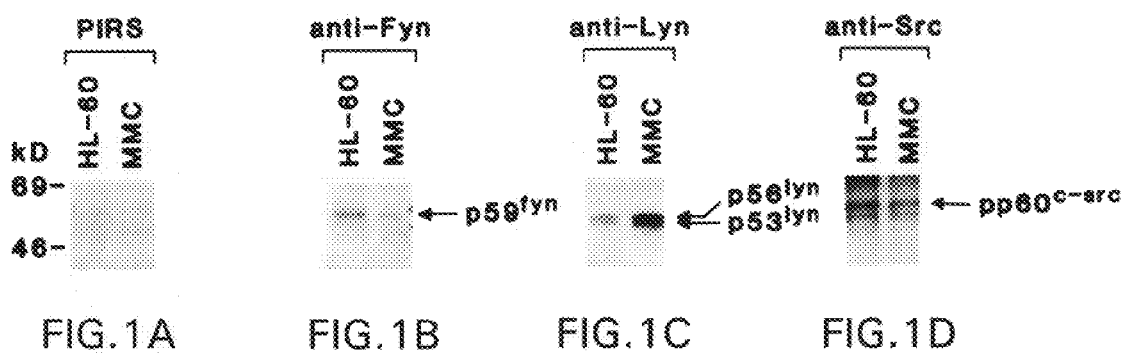
FIG. 1A, FIG. 1B, FIG. 1C and FIG. 1D. Activation of Src-like tyrosine kinases by mitomycin C (MMC). HL-60 cells were exposed to $10^{-5}$ M MMC and harvested at 1 h. Cell lysates were subjected to immunoprecipitation with pre-immune rabbit serum (PIRS) (FIG. 1A); anti-Fyn antibodies (FIG. 1B); anti-Lyn antibodies (FIG. 1C); and anti-Src antibodies (FIG. 1D). Phosphorylation reactions were performed in the presence of $[\gamma^{32}P]ATP$ for 10 min at 30° C. Phosphorylated protein was analyzed by 10% SDS-PAGE and autoradiography.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Alkylating Agents Activate the Lyn Tyrosine Kinase and Promote Tyrosine Phosphorylation of $p34^{cdc2}$ A. Materials and Methods Cell culture. HL-60 cells were grown in RPMI-1640 medium containing 15% heat-inactivated fetal bovine serum (FBS) supplemented with 100 units/ml penicillin, 100 mg/ml streptomycin, 2 mM L-glutamine, 1 mM sodium pyruvate and 1 mM non-essential amino acids. Cells were treated with MMC (Sigma Chemical Co., St. Louis, Mo.), adozelesin (Sigma), cis-platinum (Sigma), nitrogen mustard (Sigma), genistein (GIBCO/BRL, Gaithersburg, Md.), herbimycin A (GIBCO/BRL) and H-7 (Seikagaku America Inc., Rockville, Md.). Cell viability was determined by trypan blue exclusion.

Immune complex kinase assays. Cells ($2-3\times10^7$) were washed twice with ice cold phosphate buffered saline (PBS) and lysed in 2 ml of lysis buffer (20 mM Tris, pH 7.4, 150 mM NaCl, 1% NP-40, 1 mM sodium vanadate, 1 mM phenylmethylsulfonyl fluoride, 1 mM DTT and 10 mg/ml of leupeptin and aprotinin). After incubation on ice for 30 min, insoluble material was removed by centrifugation at 14000 rpm for 10 min at 4° C. Soluble proteins were precleared by incubating with 5 mg/ml rabbit-anti-mouse IgG for 1 h at 4° C. and then for an additional 30 min after addition of protein A-sepharose.

The supernatant fraction was incubated with pre-immune rabbit serum, anti-Fyn, anti-Lyn, anti-Src (UBI, Lake Placid, N.Y.) or anti-cdc2 (sc-54, Santa Cruz Biotechnology, Santa Cruz, Calif.) antibodies for 1 h at 4° C. followed by 30 min after addition of protein A-sepharose. The immune complexes were washed three times with lysis buffer and once with kinase buffer (20 mM HEPES, pH 7.0, 10 mM $MnCl_2$ and 10 mM $MgCl_2$) and resuspended in 30 ml of kinase buffer containing 1 mCi/ml [$\gamma$-$^{32}$P]ATP (3000 Ci/mmol; NEN, Boston, Mass.) with and without 5–8 mg of acid-treated enolase (Sigma). The reaction was incubated for 15 min at 30° C. and terminated by the addition of 2× SDS sample buffer. The proteins were separated in 10% SDS-polyacrylamide gels and analyzed by autoradiography. Radioactive bands were excised from certain gels and quantitated by scintillation counting.

Immune complexes were also resuspended in 30 ml kinase buffer containing 1 mCi/ml [$\gamma$-$^{32}$P]PATP and either 100 mM cdc2 peptide (amino acids 7 to 20; IEKIGEGT YGVVYK; SEQ ID NO:1) or 100 mM mutated cdc2 peptide with Phe-15 substituted for Tyr-15 (IEKIGEGTFGVVYK; SEQ ID NO:2). The reactions were incubated for 15 min at 30° C. and terminated by spotting on P81 phosphocellulose discs (GIBCO/BRL). The discs were washed twice with 1% phosphoric acid and twice with water before analysis by liquid scintillation counting.

Immunoblot analysis. Immune complexes bound to protein A-sepharose were prepared as for the autophosphorylation assays. Proteins were separated in 10% SDS-polyacrylamide gels and transferred to nitrocellulose paper. The residual binding sites were blocked by incubating the filters in 5% dry milk in PBST (PBS/0.05% Tween-20) for 1 h at room temperature. The blots were subsequently incubated with anti-cdc2 or anti-phosphotyrosine (anti-P-Tyr; MAb 4G10, UBI). After washing twice with PBST, the filters were incubated for 1 h at room temperature with anti-mouse IgG (whole molecule) peroxidase conjugate (Sigma) in 5% milk/PBST. The filters were then washed and the antigen-antibody complexes visualized by the ECL detection system (Amersham, Arlington Heights, Ill).

Coimmunoprecipitation. Immunoprecipitations were performed with anti-$p34^{cdc2}$ at 5 mg/ml cell lysate. Immune complexes were collected on protein A-Sepharose beads (Pharmacia), washed three times with lysis buffer and twice with kinase buffer, resuspended in kinase buffer and then incubated for 10 min at 30° C. in the presence of 1 mCi/ml [$\gamma$-$^{32}$P]ATP. One aliquot of the kinase reaction was subjected to SDS-PAGE and autoradiography. The other aliquot was washed in lysis buffer to remove free ATP and then boiled in 20 mM Tris-HCl, pH 8.0 containing 0.5% SDS and 1 mM DTT to disrupt protein-protein interaction. After dilution to 0.1% SDS, a secondary immunoprecipitation was then performed by adding anti-Lyn antibody and protein A-Sepharose beads. The anti-Lyn immunoprecipitates were then subjected to SDS-PAGE and autoradiography.

Fusion protein binding assays. The plasmid encoding a glutathione S-transferase (GST)-Lyn (amino acids 1 to 243) fusion protein was obtained from T. Pawson, Toronto, Canada and transfected into E. coli DH5a (Pleiman et al., 1993). The fusion protein was induced with IPTG, purified by affinity chromatography using glutathione-Sepharose beads (Pharmacia) and equilibrated in lysis buffer. HL-60 cell lysates were incubated with 50 mg immobilized GST or GST-Lyn for 2 h at 40° C. The protein complexes were washed three times with lysis buffer and boiled for 5 min in SDS sample buffer. The complexes were then separated in 10% SDS-PAGE and subjected to silver staining or immunoblot analysis with anti-cdc2.

B. Results

Previous studies have demonstrated that HL-60 cells express the $p59^{fyn}$, $p56/p53^{lyn}$ and $pp60^{c-src}$ tyrosine kinases (Barnekow & Gessler, 1986; Gee et al., 1986; Katagiri et al., 1991). In this example, the inventors have shown that certain of these tyrosine kinases are activated during treatment of HL-60 cells with MMC.

Immunoprecipitates from control and MMC-treated cells were assayed for autophosphorylation. There was no detectable kinase activity in precipitates obtained with pre-immune rabbit serum (FIG. 1A). Other studies with an anti-Fyn antibody demonstrated that autophosphorylation of $p59^{fyn}$ is decreased at 1 h of MMC treatment (FIG. 1B). Similar results were obtained at multiple time points through 6 h of MMC exposure. In contrast, immunoprecipitates with anti-Lyn demonstrated an increase in $p56/p531^{lyn}$ activity as a result of MMC exposure (FIG. 1C). The finding that anti-Src immunoprecipitates also exhibited a decrease in $pp60^{c-src}$ activity in MMC-treated cells (FIG. 1D) suggests that MMC exposure is associated with selective activation of $p56/p53^{lyn}$.

Figure 2A:
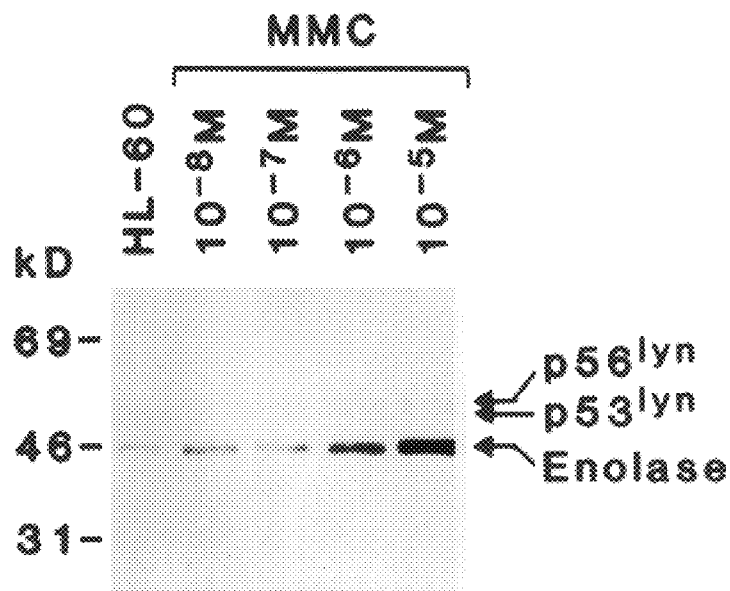
FIG. 2A, FIG. 2B and FIG. 2C. Activation of $p56/p53^{lyn}$ kinase by MMC.
Figure 2B:
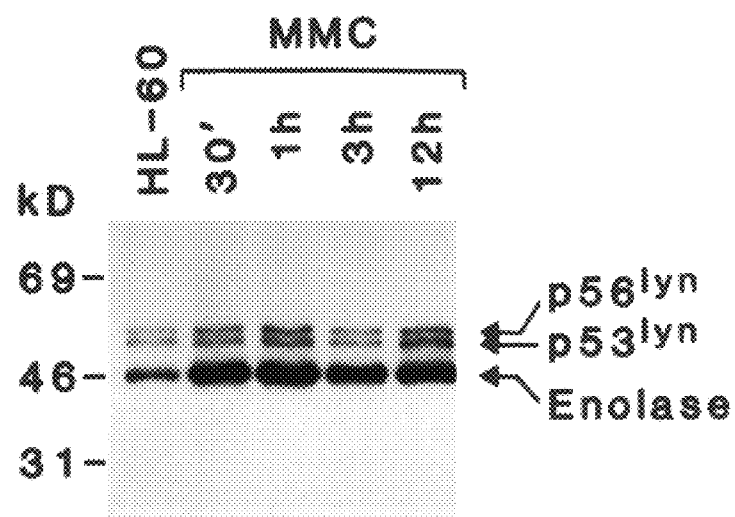

Activation of $p56/p53^{lyn}$ was confirmed at different concentrations of MMC and by assaying for phosphorylation of the substrate protein enolase. Increases in $p56/p53^{lyn}$ activity were found at $10^{-8}$ and $10^{-7}$ M MMC, while more pronounced stimulation of this kinase was apparent at $10^{-6}$ and $10^{-5}$ M (FIG. 2A). The results further demonstrate that p56/p53$^{lyn}$ activity is rapidly induced in MMC-treated cells. Increases in MMC-induced phosphorylation of p56/p53$^{lyn}$ and enolase were first detectable at 30 min (4.2-fold increase for enolase) and persisted through at least 12 h (4.1-fold for enolase) of drug exposure (FIG. 2B). The induction of p56/p53$^{lyn}$ activity was not related to cell death since viability as determined by trypan blue exclusion was >90% at 12 h of MMC treatment.

Figure 2C:
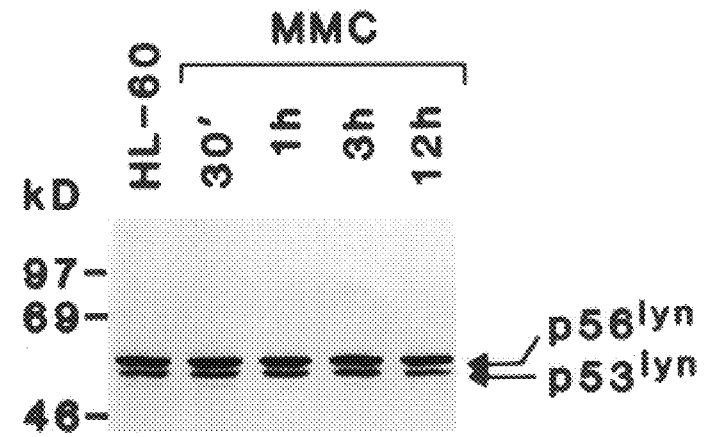

Immunoblot analysis was also performed to determine whether the increases in p56/p53$^{lyn}$ activity were due to a greater abundance in protein. The results demonstrate similar levels of p56/p53$^{lyn}$ protein (FIG. 2C). These findings supported a rapid and prolonged activation of p56/p53$^{lyn}$ in response to MMC treatment.

Figure 3A:
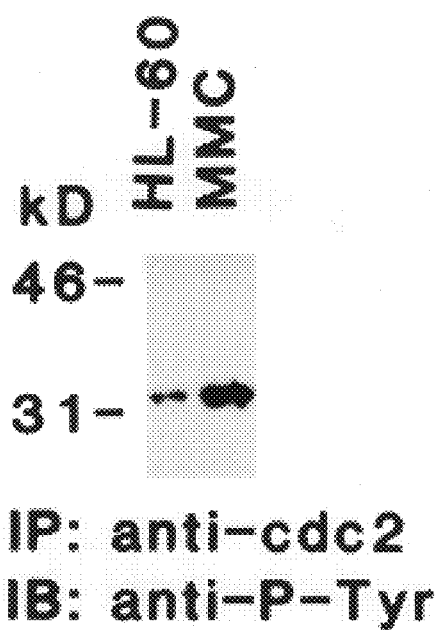
FIG. 3A and FIG. 3B. Tyrosine phosphorylation of p56/p53$^{lyn}$ in MMC-treated cells. HL-60 cells were treated with MMC for 1 h. Cell lysates were immunoprecipitated with anti-Lyn and the immunoprecipitates were subjected to immunoblotting with anti-P-Tyr (FIG. 3A) or anti-Lyn (FIG. 3B).
Figure 3B:
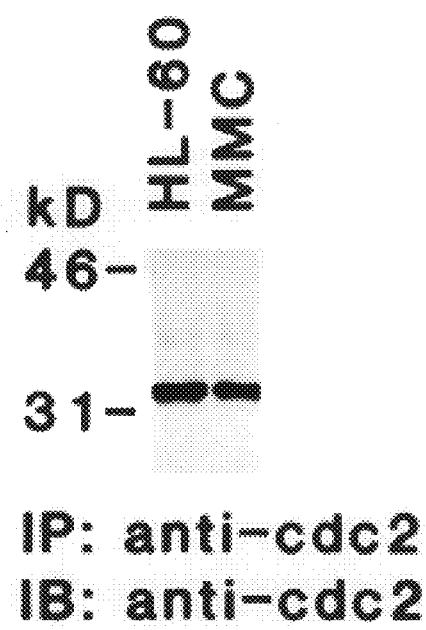

In order to confirm that activation of p56/p53$^{lyn}$ is associated with tyrosine phosphorylation, the anti-Lyn immune complexes were assayed by immunoblotting with anti-P-Tyr. The results demonstrate an increase in tyrosine phosphorylation of p56/p53$^{lyn}$ from MMC-treated as compared to control cells (FIG. 3A). Analysis of the anti-Lyn immunoprecipitates by immunoblotting with anti-Lyn confirmed the presence of similar levels of protein after MMC treatment (FIG. 3B).

Figure 4A:
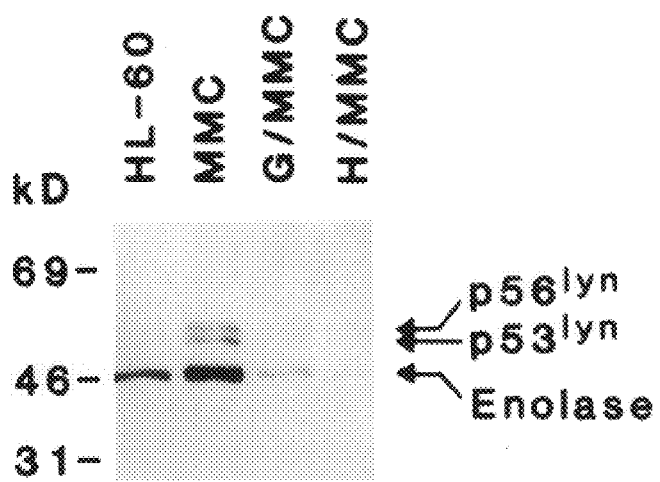
FIG. 4A, FIG. 4B and FIG. 4C. MMC-induced p56/p53$^{lyn}$ activation is sensitive to tyrosine kinase inhibitors and is not a direct effect.
Figure 4B:
Figure 4C:
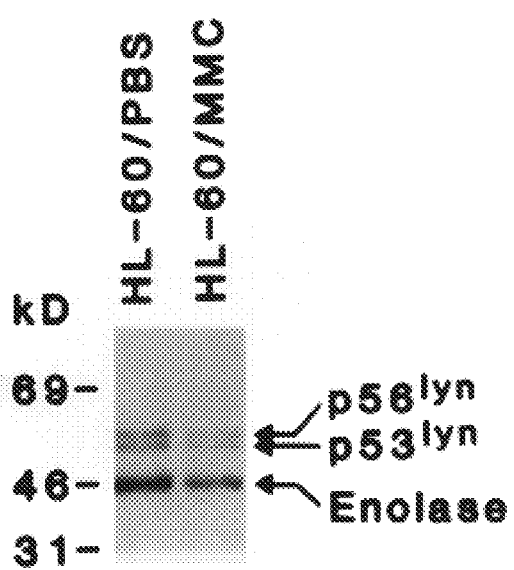

The involvement of tyrosine phosphorylation was further supported by the demonstration that pretreatment of cells with the tyrosine kinase inhibitors, genistein (Akiyama et al., 1987) and herbimycin A (Uehara et al., 1989) completely blocks the stimulation of p56/p53$^{lyn}$ activity associated with MMC treatment (FIG. 4A). In contrast, pretreatment with the isoquinoline sulfonamide inhibitor of serine/threonine protein kinases, H-7 (Hidaka et al., 1984), had no detectable effect on the MMC-induced activity (FIG. 4B). These effects of MMC on induction of p56/p53$^{lyn}$ could be related to direct interaction of this agent with Lyn kinase. However, incubation of anti-Lyn immune complexes in the presence of MMC was associated with a decrease in kinase activity (FIG. 4C). Taken together, these findings indicated that MMC induces the tyrosine kinase activity of p56/p53$^{lyn}$ by an indirect mechanism.

Figures 5A, 5B, 5C:
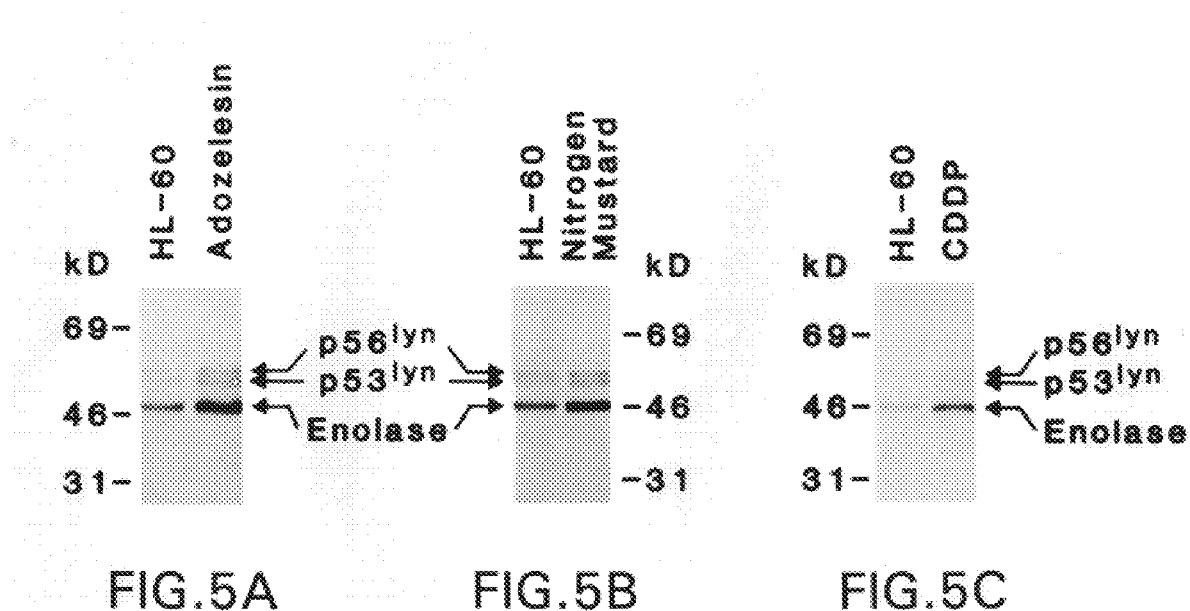
FIG. 5A, FIG. 5B and FIG. 5C. Other alkylating agents active p56/p53$^{lyn}$. HL-60 cells were treated with $2 \times 10^{-6}$ M adozelesin (FIG. 5A), $10^{-5}$ M nitrogen mustard (FIG. 5B) and $10^{-5}$ M cis-platinum (FIG. 5C) for 1 h. Anti-Lyn immunoprecipitates were analyzed for phosphorylation of p56/p53$^{lyn}$ and enolase.

The available evidence indicates that MMC acts as a monofunctional and bifunctional alkylating agent (Carrano et al., 1979). Consequently, adozelesin, another monofunctional but structurally distinct alkylating agent (Bhuyan et al., 1992; Hurley et al., 1984), was investigated. The results demonstrate that treatment of HL-60 cells with adozelesin is similarly associated with stimulation of p56/p53$^{lyn}$ and enolase phosphorylation (FIG. 5A). Other studies were performed with agents that also induce the formation of DNA cross-links. Nitrogen mustard, an agent that forms monoadducts and DNA interstrand cross-links (Ewig & Khon, 1977; Hartley et al., 1992), was effective in inducing p56/p53$^{lyn}$ activity (FIG. 5B) Moreover, treatment of cells with cis-platinum, an agent that forms intrastrand cross-links (Sherman & Lippard, 1987), was associated with stimulation of the p56/p53$^{lyn}$ kinase (FIG. 5C). These findings indicated that the response of cells to diverse alkylating-type agents induces activation of p56/p53$^{lyn}$.

In order to examine the significance of p56/p53$^{lyn}$ activation, the association of this kinase with specific intracellular proteins that undergo tyrosine phosphorylation in MMC-treated cells was investigated. This issue was initially addressed using a GST-Lyn fusion protein to identify molecules which interact with p56/p53$^{lyn}$. Lysates from MMC-treated cells were incubated with immobilized GST or GST-Lyn. Analysis of the adsorbates by SDS-PAGE and staining demonstrated the presence of a 34 kD protein.

Figure 6A:
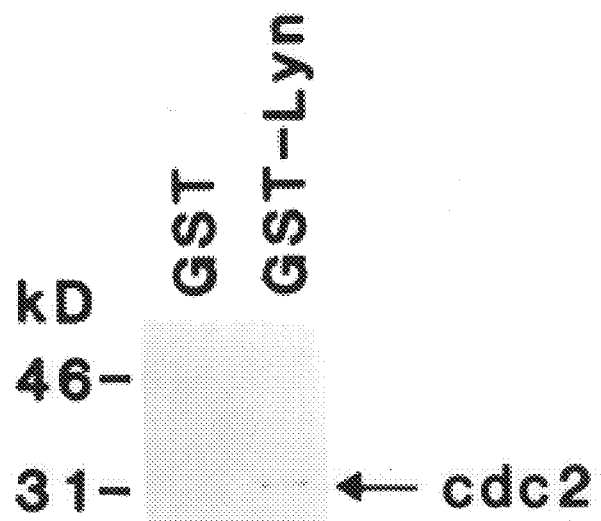
FIG. 6A and FIG. 6B. Association of p56/p53$^{lyn}$ and p34$^{cdc2}$. HL-60 cells were treated with $10^{-5}$ M MMC for 1 h.
Figure 6B:
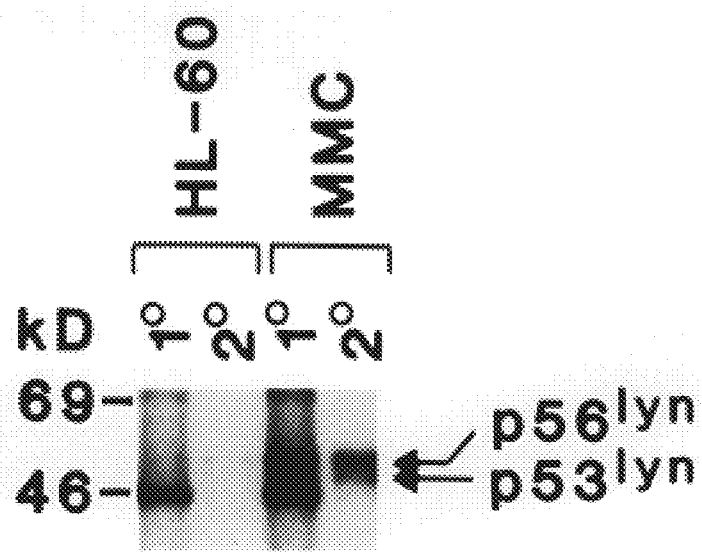

The inventors assayed the adsorbates for reactivity with anti-cdc2. The results indicate that p34$^{cdc2}$ associates with the GST-Lyn fusion protein and not the GST control (FIG. 6A). The potential interaction between p56/p53$^{lyn}$ and p34$^{cdc2}$ was further examined in coimmunoprecipitation studies. Lysates of control and MMC-treated cells were subjected to immunoprecipitation with anti-cdc2 and the immunoprecipitates were assayed for autophosphorylation (FIG. 6B). One aliquot of the in vitro kinase reaction was assayed by SDS-PAGE and autoradiography. While immunoprecipitates from MMC-treated cells exhibited phosphorylation of 53-56 kD proteins, there was little if any of this activity in control cells (FIG. 6B). In order to determine whether the anti-cdc2 immunoprecipitates contain p56/p53$^{lyn}$, the other aliquot of the in vitro kinase reaction was treated to disrupt protein complexes and then subjected to immunoprecipitation with anti-Lyn. The results demonstrate increased levels of autophosphorylated p56/p53$^{lyn}$ when assaying MMC-treated as compared to control cells (FIG. 6B).

Figure 7A:
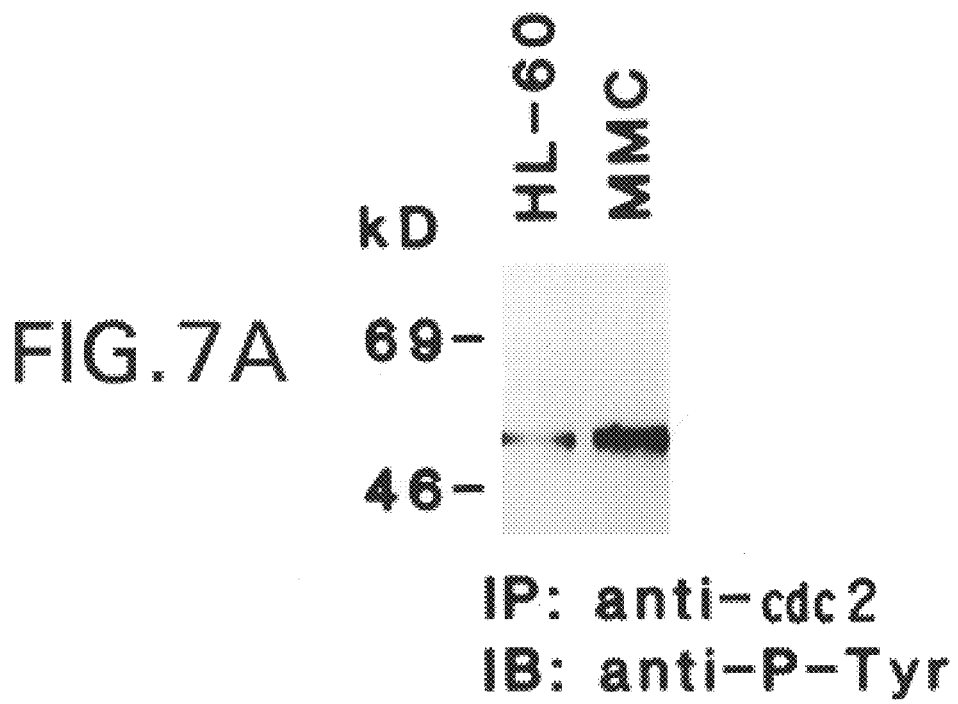
FIG. 7A and FIG. 7B. Effects of MMC treatment on tyrosine phosphorylation of p34$^{cdc2}$. HL-60 cells were exposed to MMC for 1 h.
Figure 7B:
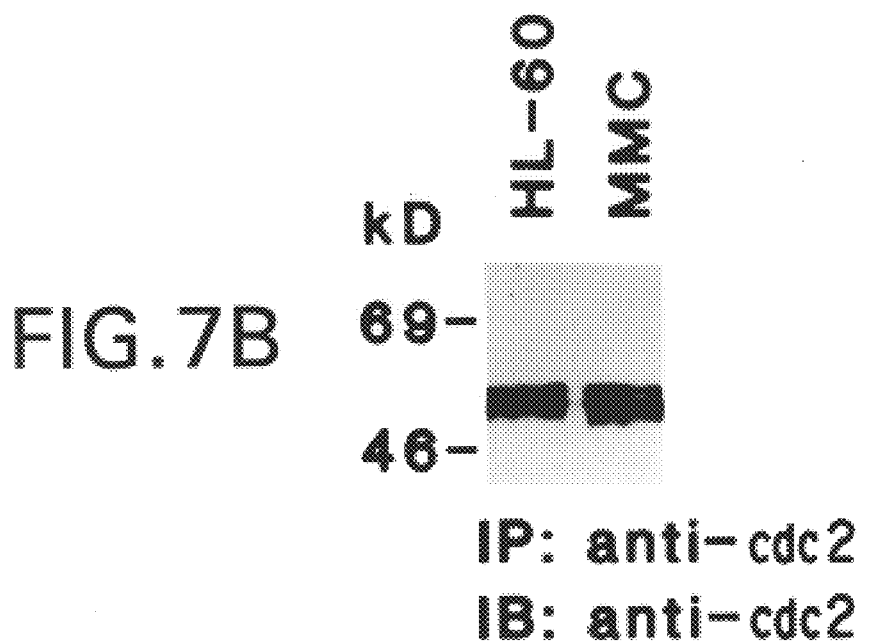

The finding that MMC exposure induces an interaction between p56/p53$^{lyn}$ and p34$^{cdc2}$ prompted further studies to determine whether p34$^{cdc2}$ exhibits increased tyrosine phosphorylation in MMC-treated cells. Immunoprecipitation of p34$^{cdc2}$ and then immunoblotting of the precipitates with anti-P-Tyr demonstrated an increase in reactivity as a result of MMC treatment (FIG. 7A). Reprobing the filter with the anti-cdc2 antibody demonstrated similar levels of p34$^{cdc2}$ protein (FIG. 7B). Since these findings indicated that MMC treatment is associated with increased tyrosine phosphorylation of p34$^{cdc2}$, other studies were performed to determine whether p56/p53$^{lyn}$ can phosphorylate p34$^{cdc2}$ in vitro.

Figure 8:
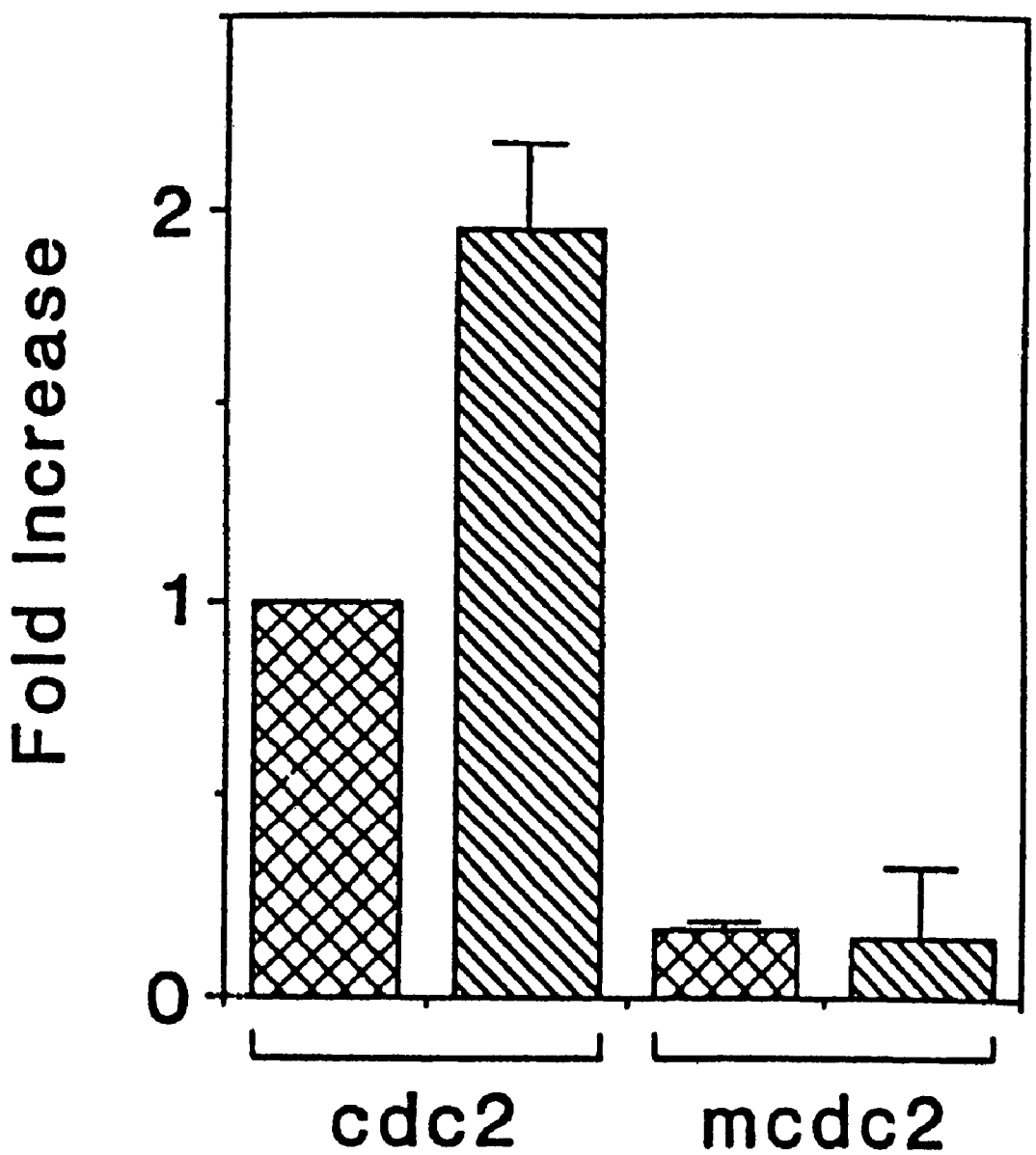
FIG. 8. Phosphorylation of cdc2 peptides by p56/p53$^{lyn}$. HL-60 cells were treated with MMC for 1 h. Cell lysates were subjected to immunoprecipitation with anti-Lyn. The immunoprecipitates were assayed for phosphorylation of either a cdc2 (IEKIGEGTYGVVY SEQ ID NO:1) or mutated cdc2 (mcdc2; Y-15 to F-15) peptide. The results represent the mean ± S.D. of two independent studies each performed in duplicate and are normalized to control phosphorylation of the cdc2 peptide. Control cells (cross hatch); MMC-treated cells (stripes).

In order to study a potential phosphorylation site for Src-like kinases located at Tyr-15 of p34$^{cdc2}$, synthetic peptides were prepared with sequences derived from amino acids 7 to 20 of p34$^{cdc2}$ and another with substitution at Tyr-15 with Phe-15. While anti-Lyn immune complexes from control cells phosphorylated the cdc2 peptide, similar complexes from MMC-treated cells exhibited nearly a 2-fold stimulation in this activity (FIG. 8). In contrast, there was little phosphorylation of the mutated cdc2 peptide with anti-Lyn complexes from control or MMC-treated cells (FIG. 8). These findings indicated that p56/p53$^{lyn}$ phosphorylates the Tyr-15 site of p34$^{cdc2}$.

The present results demonstrate that treatment of HL-60 cells with MMC is associated with selective activation of the p56/p53$^{lyn}$ tyrosine kinase. These findings are not limited to HL-60 cells since other cell lines, for example U-937 myeloid leukemia cells, also respond to this agent with increases in p56/p53$^{lyn}$ activity.

The lyn gene encodes two forms of the tyrosine kinase, p56$^{lyn}$ and p53$^{lyn}$, due to alternate mRNA splicing (Yamanashi et al., 1987; Yamanashi et al., 1989). As a member of the Src-like family of tyrosine kinases, p56/p53$^{lyn}$ is related to pp60$^{c-src}$ and p59$^{fyn}$ (Cantley et al., 1991). However, only p56/p53$^{lyn}$ was activated in MMC-treated cells. These kinases are often associated with cell surface receptors at the interface between the cell membrane and cytoplasm. Studies of p56/p53$^{lyn}$ in B cells have demonstrated an association with the B-cell antigen receptor (Pleiman et al., 1993; Yamanashi et al., 1992). Engagement of the B-cell antigen receptor induces activation of p56/p53$^{lyn}$, as well as other Src-like kinases, and tyrosine phosphorylation of substrates that include PLCg2, MAP kinase and GAP (Pleiman et al., 1993). Other studies have shown that p56/p53$^{lyn}$ associates with the 85 kDa a-subunit of PI 3-K and induces PI 3-K activity (Yamanashi et al., 1992).

Thus, p56/p53$^{lyn}$ is capable of associating with and phosphorylating diverse downstream effector molecules.

Although the cellular effects of alkylating agents such as MMC are generally attributed to DNA damage, their action may be related to alkylation of RNA or protein. The demonstration that MMC treatment of intact cells is associated with activation of p56/p53$^{lyn}$ raised the possibility that this effect might be due to direct alteration of Lyn protein. p56/p53$^{lyn}$ activity was however decreased in vitro by incubation of anti-Lyn immune complexes with MMC. In order to address the possibility that MMC-induced activation of p56/p53$^{lyn}$ is related to formation of DNA lesions, another agent, adozelesin, was used that covalently binds to the N-3 of adenine within the minor groove of DNA (Bhuyan et al., 1992; Hurley et al., 1984). Adozelesin also induces p56/p53$^{lyn}$ activity.

HL-60 cells also respond similarly to other alkylating agents, such as nitrogen mustard which reacts predominantly with guanines by alkylation of their N-7 positions or forms DNA interstrand cross-links (Ewig & Khon, 1977; Hartley et al., 1992). Moreover, p56/p53$^{lyn}$ activity was stimulated by cis-platinum which induces intrastrand cross-links (Sherman & Lippard, 1987). Thus, structurally distinct agents that damage DNA by diverse mechanisms are capable of inducing p56/p53$^{lyn}$ activity. Recent studies have demonstrated that treatment of HeLa cells with ultraviolet (UV) irradiation is associated with increases in the catalytic activity of c-Src and c-Fyn, but not that of c-Yes (Devary et al., 1992). Taken together with the absence of detectable pp60$^{c\text{-}src}$ or p$_{59}^{fyn}$ activation in MMC-treated HL-60 cells, these results suggest that induction of these tyrosine kinases may be cell-type or agent specific.

The p34$^{cdc2}$ serine/threonine protein kinase controls entry of cells into mitosis (Nurse, 1990; Pines & Hunter, 1990). This kinase is regulated by networks of kinases and phosphatases that appear to respond to the state of DNA replication. Activation of p34$^{cdc2}$ involves association with cyclin B and posttranslational modifications of the p34$^{cdc2}$/cyclin B complex (Norbury & Nurse, 1992). Phosphorylation of p34$^{cdc2}$ on Thr-161 is required for activation (Atherton-Fessler et al., 1993; Desai et al., 1992; Solomon et al., 1992), while Tyr-15 phosphorylation results in inhibition of both p34$^{cdc2}$ activity and entry of cells into mitosis (Gould & Nurse, 1989; Gould et al., 1990).

Studies have demonstrated that treatment of mammalian cells with alkylating and other DNA-damaging agents is associated with G$_2$ arrest (Konopa, 1988; Lau & Pardee, 1982; Tobey, 1975). However, the precise mechanisms responsible for this effect have remained unclear. Exposure of cells to ionizing radiation is associated with rapid inhibition of p34$^{cdc2}$ activity and G$_2$ arrest (Lock & Ross, 1990). Other studies have demonstrated that arrest of nitrogen mustard-treated cells at G$_2$ is temporally related to formation of DNA cross-links and p$_{34}^{cdc2}$ inhibition (O'Connor et al., 1992). In the present studies, it is demonstrated that MMC treatment results in rapid tyrosine phosphorylation of p34$^{cdc2}$. Similar findings have been obtained in cells treated with ionizing radiation (see following Examples). This modification of p34$^{cdc2}$ is associated with loss of kinase activity as determined by assaying anti-cdc2 immunoprecipitates for phosphorylation of Hi histone. Thus, the phosphorylation of p34$^{cdc2}$ on tyrosine appears to represent in part the response of mammalian cells to DNA damage and may contribute to G$_2$ arrest by inhibition of p34$^{cdc2}$ activity.

The available evidence indicates that the p107$^{weel}$ dual-specificity kinase is responsible for phosphorylation of p34$^{cdc2}$ on Tyr-15 (Featherstone & Russell, 1991; Parker et al., 1991; Parker et al., 1992). While p107$^{weel}$ appears to control p34$^{cdc2}$ activity to ensure completion of S-phase, other studies suggest that p107$^{wee}$ is not required for the DNA-damage-dependent mitotic checkpoint. In this context, normal mitotic arrest has been observed after irradiation of Schizosaccharomyces pombe cells with a defective or missing weel gene (Barbet & Carr, 1993). Other studies have shown that p34$^{cdc2}$ is phosphorylated on tyrosine in yeast weel minus mutants (Gould et al., 1990). The present results in mammalian cells suggest that regulation of p34$^{cdc2}$ following exposure to alkylating agents involves activation of p56/p53$^{lyn}$. The association of p56/p53$^{lyn}$ and p34 $^{cdc2}$ in MMC-treated cells, as well as the finding that p56/p53$^{lyn}$ can phosphorylate the Tyr-15 site of p34$^{cdc2}$ in vitro, support the possibility that p56/p53$^{lyn}$ contributes to signaling from the mitotic checkpoint that monitors for alkylating agent-induced damage.

EXAMPLE II

Ionizing Radiation Activates the Lyn Tyrosine Kinase and Promotes Tyrosine Phosphorylation of p34$^{cdc2}$ Treatment of human HL-60 myeloid leukemia cells with ionizing radiation is associated with activation of the Lyn tyrosine kinase. The lyn gene encodes two forms of this kinase, p56$^{lyn}$ and p53$^{lyn}$, as a result of alternate splicing (Yamanashi et al., 1987; 1989). Both p56/p53$^{lyn}$, but not certain other Src-related kinases, are activated in irradiated HL-60 cells. Activation of p56/p53$^{lyn}$ represents a signaling pathway distinct from those involved in X-ray-induced early response gene expression.

HL-60 myeloid leukemia cells were grown in RPMI-1640 medium containing 15% heat-inactivated fetal bovine serum (FBS) supplemented with 100 units/ml penicillin, 100 mg/ml streptomycin, 2mM L-glutamine, 1mM sodium pyruvate and 1mM non-essential amino acids. Cells in logarithmic growth phase were suspended in complete RPMI-1640 medium with 0.5% FBS 18 hours prior to irradiation.

Irradiation was performed at room temperature using a Gammacell 1000 (Atomic Energy of Canada, Ottawa) under aerobic conditions with a $^{137}$Cs source emitting at a fixed dose rate of 13.3 Gy/min as determined by dosimetry. HL-60 cells were also treated with 50 mM H$_2$O$_2$ (Sigma Chemical Co., St. Louis, Mo.), 30 mM N-acetyl cysteine (NAC; Sigma), 10 μM genistein (GIBCO/BRL, Gaithersburg, MD) or 10 μM herbimycin A (GIBCO/BRL).

Cells (2–3×10$^7$) were washed twice with ice cold phosphate buffered saline (PBS) and lysed in 2 ml of lysis buffer (20 mM Tris, pH 7.4, 150 mM NaCl, 1% NP-40, 1 mM sodium vanadate, 1 mM phenylmethylsulfonyl fluoride, 1 mM DTT, and 10 mg/ml of leupeptin and aprotinin). After incubation on ice for 30 min, insoluble material was removed by centrifugation at 1400 rpm for 10 min at 4° C. Soluble proteins were precleared by incubation with 5mg/ml rabbit anti-mouse IgG for 1 hour at 4° C. and then addition of protein A sepharose for 30 min.

The supernatants were incubated with 2.5 μl of anti-human Fyn, 2 μl of anti-human Lyn, 3 μl of anti-human Lyk (N-terminal) or 3 μl of anti-Src antibody (UBI, Lake Placid, N.Y.) for 1 hour at 4° C. followed by 30 min with protein A-sepharose. The immune complexes were washed three times with lysis buffer, once with kinase buffer (20 mM HEPES, pH 7.0, 10 mM MnCl$_2$ and 10 mM MgCl$_2$) and resuspended in 30 μl of kinase buffer containing 1 mCi/ml [γ-$^{32}$P]ATP (3000 Ci/mmol; NEN, Boston, Mass.). The reaction was incubated for 10 min at 30° C. and terminated by the addition of 2× SDS sample buffer. The proteins were resolved in 10% SDS-polyacrylamide gels, dried and analyzed by autoradiography.

Immune complexes as prepared for autophosphorylation assays were washed three times with lysis buffer and once with kinase buffer. The beads were resuspended in 30 μl of kinase buffer containing 1 mCi/ml [γ-$^{32}$p]ATP and 3–5 mg of acid treated enolase (Sigma). The reaction was incubated for 10 min at 30° C. and terminated by the addition of 2× SDS sample buffer. The proteins were resolved by 10% SDS-PAGE. Equal loading of the enolase was determined by staining with Coomassie blue. The gels were then destained and analyzed by autoradiography. Radioactive bands were also excised from the gel and quantitated by scintillation counting.

Figures 9A, 9B, 9C:
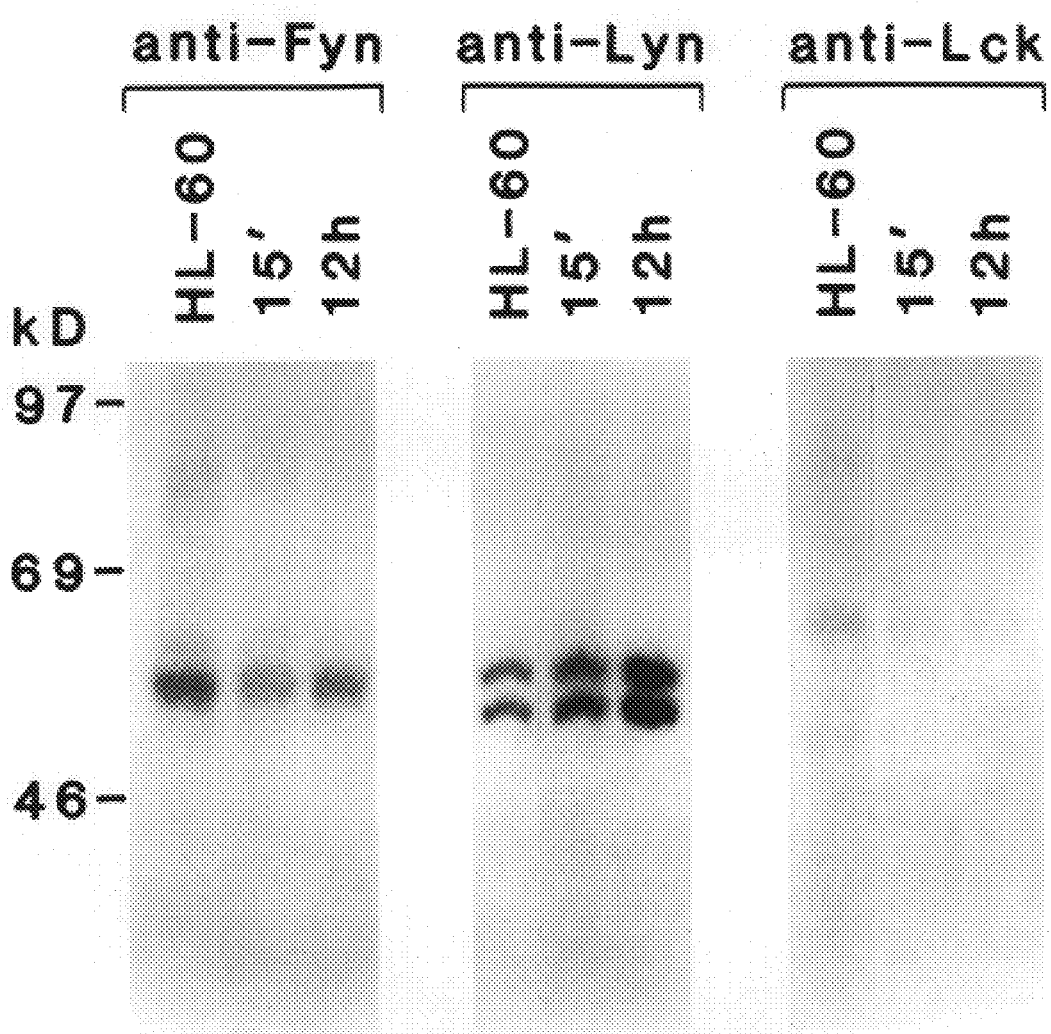
FIG. 9A, FIG. 9B and FIG. 9C. Activation of Src-like protein tyrosine kinases by ionizing radiation. HL-60 cells were exposed to 200 cGy ionizing radiation and harvested at 15 min or 2 hours.

Previous studies have demonstrated that p59$^{fyn}$ and p56/p53$^{lyn}$ are expressed in HL-60 cells (Katagiri et al., 1991). Using autophosphorylation assays, the present inventors herein show that irradiation of HL-60 cells with 200 cGy was associated with little if any change in p59$^{fyn}$ activity at 15 min and 12 hours (FIG. 9A). A more detailed analysis between those time points revealed similar findings. In contrast, p56/p53$^{lyn}$ activity was increased at both 15 min and 12 hours after irradiation as compared to that in untreated cells (FIG. 9B). Studies of p56$^{lck}$ demonstrated little detectable activity in HL-60 cells before or after exposure to ionizing radiation (FIG. 9C). These findings show that p56/p53$^{lyn}$ is selectively activated in HL-60 cells by ionizing radiation. This conclusion is further supported by the absence of an increase in c-Src activity following irradiation.

Figure 10A:
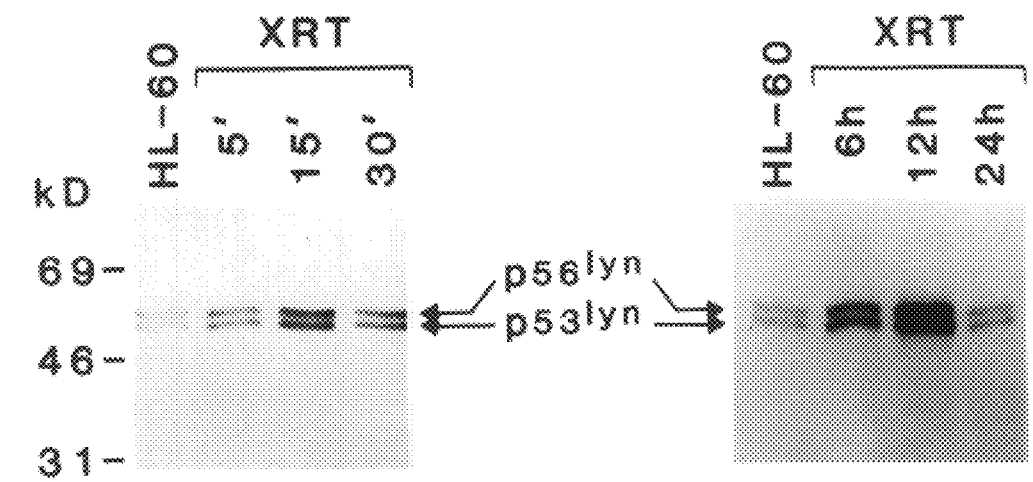
FIG. 10A and FIG. 10B. Activation of p53/56$^{lyn}$ kinase by ionizing radiation. HL-60 cells were exposed to 200 cGy ionizing radiation for 5 min, 15 min, 30 min, 6 hours, 12 hours, or 24 hours. Cell lysates were subjected to immunoprecipitation with anti-Lyn.

HL-60 cells were also irradiated with 200 cGy and immunoprecipitates assayed for both p56/p53$^{lyn}$ autophosphorylation and enolase (a substrate protein) phosphorylation. Irradiation was associated with an increase in p56/p53$^{lyn}$ autophosphorylation at 5 min that persisted through 12 hours (FIG. 10A). However, assays at 24 hours after X-ray treatment revealed declines in p56/p53$^{lyn}$ signals (FIG. 10A).

Figure 10B:
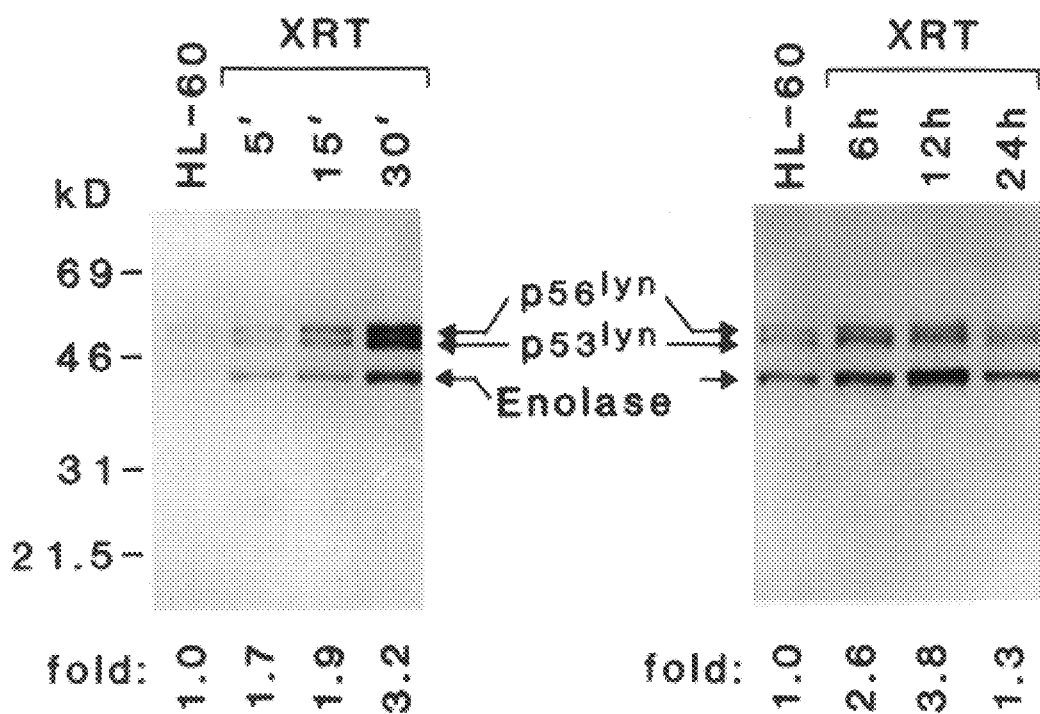

Similar findings were obtained when using enolase as the substrate. While stimulation of p56/p53$^{lyn}$ autophosphorylation was less apparent under these conditions, increases in enolase phosphorylation were clearly detectable when comparing anti-Lyn immunoprecipitates from control and irradiated HL-60 cells (FIG. 10B). This increase in activity was rapid and sustained for at least 12 hours (FIG. 10B). Quantitation of $^{32}$P-incorporation into enolase by scintillation counting demonstrated X-ray-induced increases in p56/p53$^{lyn}$ activity of approximately 3-fold at 15 min to 12 hours (FIG. 10B). As observed in autophosphorylation studies, enolase phosphorylation was also decreased at 24 hours (FIG. 10B).

Figure 11:
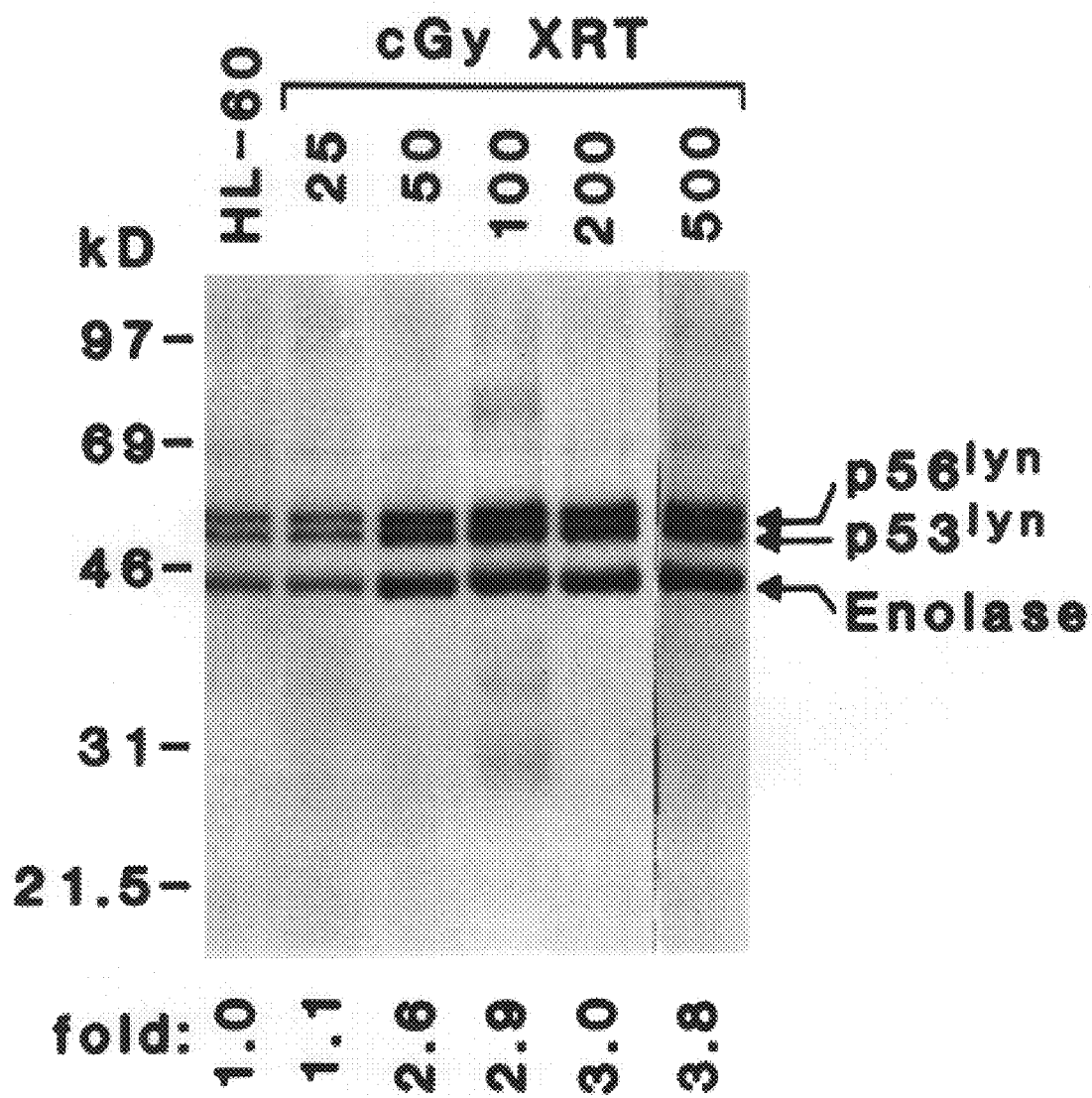
FIG. 11. Different doses of ionizing radiation induce activation of p53/p56$^{lyn}$. HL-60 cells were exposed to the indicated doses of ionizing radiation and then harvested at 12 h. Soluble proteins were subjected to immunoprecipitation with anti-Lyn. The immunoprecipitates were analyzed for phosphorylation of p56/p53$^{lyn}$ and enolase. The fold increase in enolase phosphorylation is indicated at the bottom.

Similar studies were performed at different doses of ionizing radiation (FIG. 11). Treatment with 25 cGy had little if any effect on phosphorylation of p56/p53$^{lyn}$ or enolase. Doses of 50 cGy, however, were associated with increases in p56/p53$^{lyn}$ activity (FIG. 11). Moreover, on the basis of enolase phosphorylation there was an apparent dose-dependent stimulation of this kinase (FIG. 11).

The cellular effects of ionizing radiation are believed to be related to direct interaction of X-rays with DNA or through the formation of reactive oxygen intermediates (ROIs) which damage DNA and cell membranes (Hall, 1988). While the role of different classes of ROIs in activation of the Src-like kinases is unclear, recent studies have demonstrated that $H_2O_2$ and diamide, which oxidize free sulfhydryl groups in cells, activate p$_{56}$$^{lck}$ in T cells (Nakamura et al., 1993).

Figure 12A:
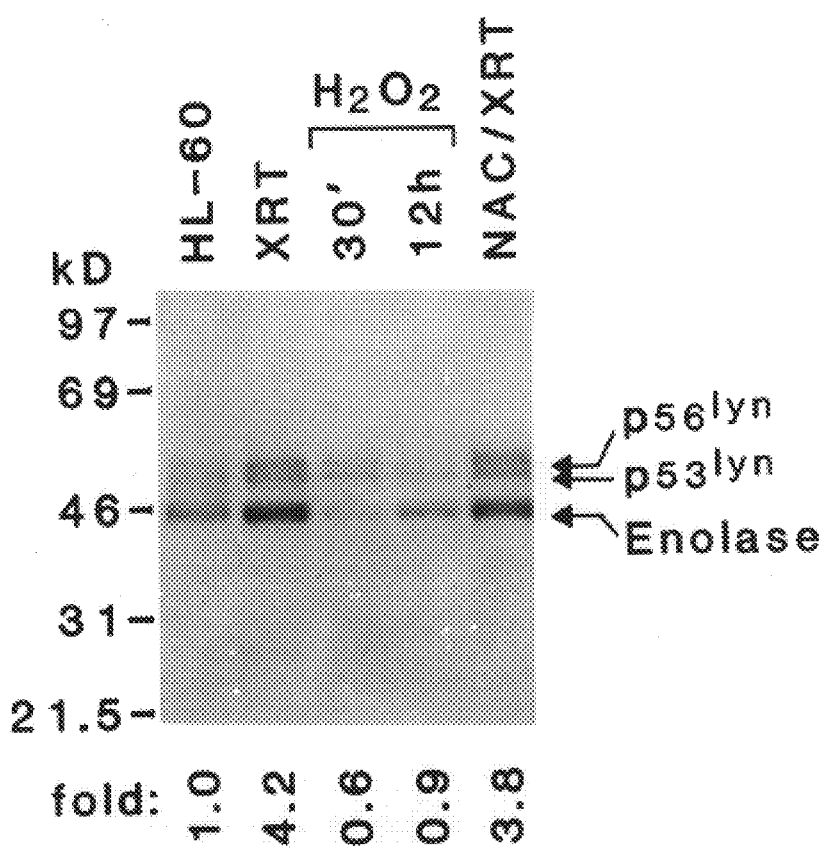
FIG. 12A and FIG. 12B. Effects of $H_2O_2$, NAC and protein tyrosine kinase inhibitors on activation of p56/p53$^{lyn}$.

HL-60 cells were either treated with $H_2O_2$ for the indicated times or pretreated with 30 mM NAC for 1 hour, irradiated (200 cGy) and harvested at 12 hours. Irradiated HL-60 cells treated with $H_2O_2$ did not show a detectable increase in phosphorylation of p56/p53$^{lyn}$ or enolase (FIG. 12A). Cells were also treated with the antioxidant NAC (Roederer et al., 1990; Staal et al., 1990), an agent that abrogates oxidative stress by scavenging certain ROIs and increasing intracellular glutathione levels (Aruoma et al., 1989; Burgunder et al., 1989). NAC had little effect on X-ray-induced p56/p53$^{lyn}$ activity (FIG. 12A), while this agent completely blocks induction of c-jun and EGR-1 gene expression in irradiated HL-60 cells (Datta et al., 1992b; 1993).

Figure 12B:
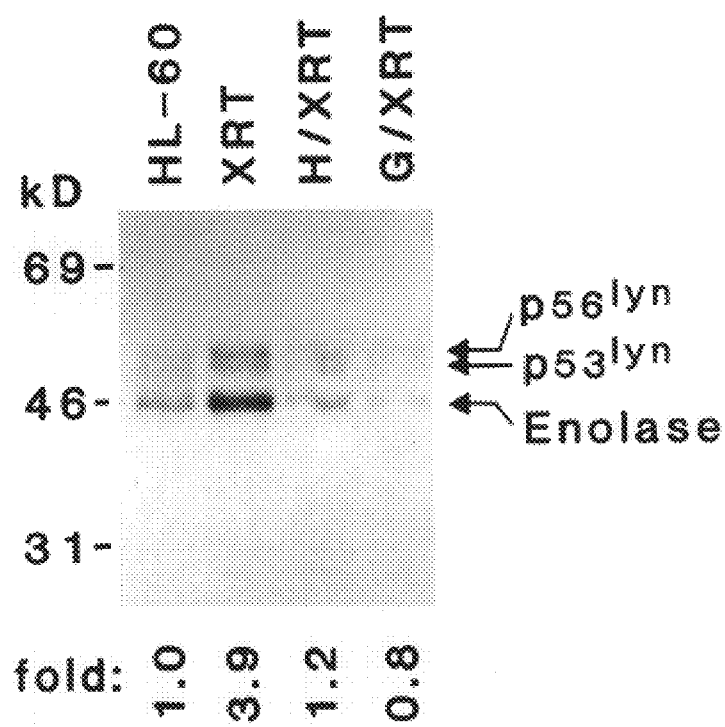

HL-60 cells were treated with 10 μM herbimycin (H) or 10 μM genistein (G) for 1 hour, irradiated (200 cGy) and then harvested at 12 hours. Cell lysates were immunoprecipitated with anti-Lyn and the immunoprecipitates were analyzed for phosphorylation of p56/p53$^{lyn}$ and enolase. In marked contrast, the tyrosine kinase inhibitors, herbimycin and genistein inhibited X-ray-induced p56/p53$^{lyn}$ activity (FIG. 12B).

Previous work has demonstrated that both ionizing radiation and $H_2O_2$ are potent inducers of c-jun gene transcription (Datta et al., 1992b). These two agents have also been used to support the role of ROIs in targeting CC(A/T)$_6$GG sequences to mediate activation of the EGR-1 gene (Datta et al., 1993). The finding that such induction of early response gene transcription is inhibited by NAC further supports the role of some of these intermediates in X-ray-induced nuclear signaling mechanisms.

The present invention provides for the activation of p56/p53$^{lyn}$ as a distinct cellular response to ionizing radiation and not to $H_2O_2$-induced oxidative stress. These findings contrast work by others which suggested that Src-like tyrosine kinases, including p56/p53$^{lyn}$, are not responsible for signaling in irradiated B cells (Uckun et al., 1992a). The demonstration that ionizing radiation, and not $H_2O_2$, induces p56/p53$^{lyn}$ activity by an NAC-insensitive mechanism therefore indicates that activation of this tyrosine kinase is independent from those signals responsible for X-ray-induced early response gene expression.

The finding in B cells that p56/p53$^{lyn}$ is functionally associated with the cell surface (Yamanashi et al., 1992) suggests that activation of this kinase by ionizing radiation may be generated near the plasma membrane rather than in the nucleus. Indeed, the available evidence supports the involvement of receptor-mediated signaling in the activation of p56/p53$^{lyn}$ (Yamanashi et al., 1992; Pleiman et al., 1993). Src-like proteins may be activated through dephosphorylation by tyrosine phosphatases (Mustalin & Altman, 1990; Cantley et al., 1991; Hartwell & Weinart, 1989) and potentially other mechanisms (Cantley et al., 1991; Hartwell & Weinart, 1989).

In regard to the effect of ionizing radiation on the phosphorylation of p34$^{cdc2}$ on tyrosine, HL-60 cells were grown in RPMI 1640 medium containing 15% heat-inactivated total bovine serum supplemented with 100 units/ml penicillin, 100 μg/ml streptomycin and 2 mM L-glutamine. Exponentially growing cells were suspended in serum free media 18 h prior to irradiation. Irradiation was performed at room temperature using a Gammacell 1000 (Atomic Energy of Canada, Ottawa) with a$^{137}$Cs source emitting at a fixed dose rate of 13.3 Gy/min as determined by dosimetry.

Cells were washed twice with ice cold phosphate buffered saline and lysed in buffer A (10 mM Tris, pH 7.4, 1 mM EGTA, 1 mM EDTA, 50 mM NaCl, 5 mM β-glycerophosphate, 1% Triton X-100, 0.5% NP-40, 1 mM sodium vanadate, 1 mM DTT, 1 mM phenylmethylsulfonyl fluoride and 10 µg/ml of leupeptin and aprotinin). Insoluble material was removed by centrifugation at 14000 rpm for 5 min at 4° C. Protein concentration was determined by Coomassie Blue staining using BSA as standard.

Soluble proteins (50 µg) were separated by electrophoresis in 10SDS-polyacrylamide gels and then transferred to nitrocellulose paper. The residual binding sites were blocked by incubating the filter in 5% dry milk in PBST (PBS/0.05% Tween 20) for 1 h at room temperature. The filters were then incubated for 1 h with either mouse anti-phosphotyrosine (anti-P-Tyr; 4G10) monoclonal antibody (4G10, UBI, Lake Placid, N.Y.) or a mouse anti-p34$^{cdc2}$ monoclonal antibody which is unreactive with other cyclin-dependent kinases (sc-54; Santa Cruz Biotechnology, Santa Cruz, Calif.). After washing twice with PBST, the blots were incubated with anti-mouse or anti-rabbit IgG peroxidase conjugate (Sigma Chemical Co., St. Louis, Mo.). The antigen-antibody complexes were visualized by chemiluminescence (ECL detection system, Amersham, Arlington Heights, Ill.).

Immunoprecipitations were performed with anti-P-Tyr or anti-p34$^{cdc2}$ at 5 µg/ml cell lysate. Immune complexes were collected with protein A-Sepharose (Pharmacia) and immunoprecipitates were analyzed by 10% SDS-PAGE. After transfer to nitrocellulose and blocking, immunoblot analysis was performed with either anti-p34$^{cdc2}$ or anti-P-Tyr and detected with the appropriate HRP-conjugated second antibody using the ECL system.

Figure 13A:
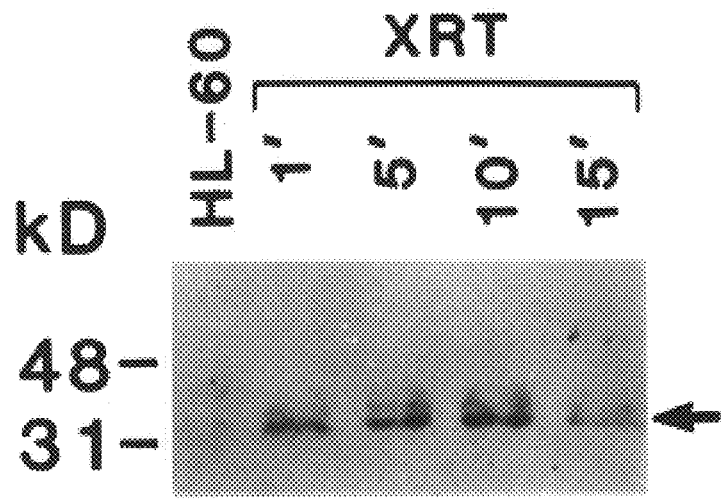
FIG. 13A and FIG. 13B. Ionizing radiation exposure induces tyrosine phosphorylation of a 34 kD substrate. HL-60 cells were exposed to 200 cGy ionizing radiation and harvested at the indicated times.
Figure 13B:
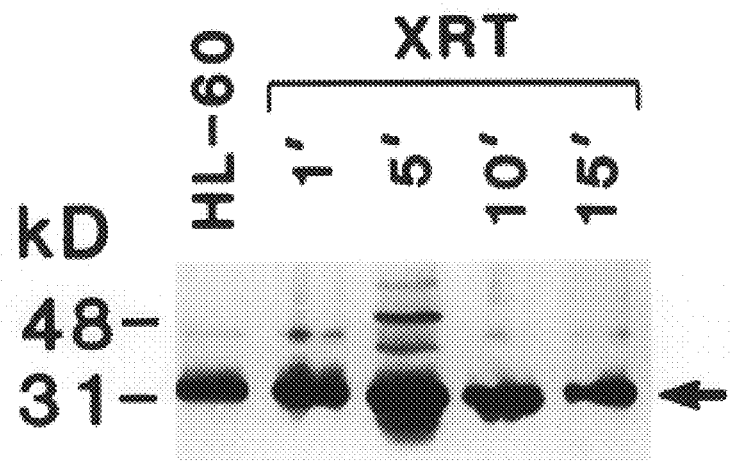
Figure 14A:
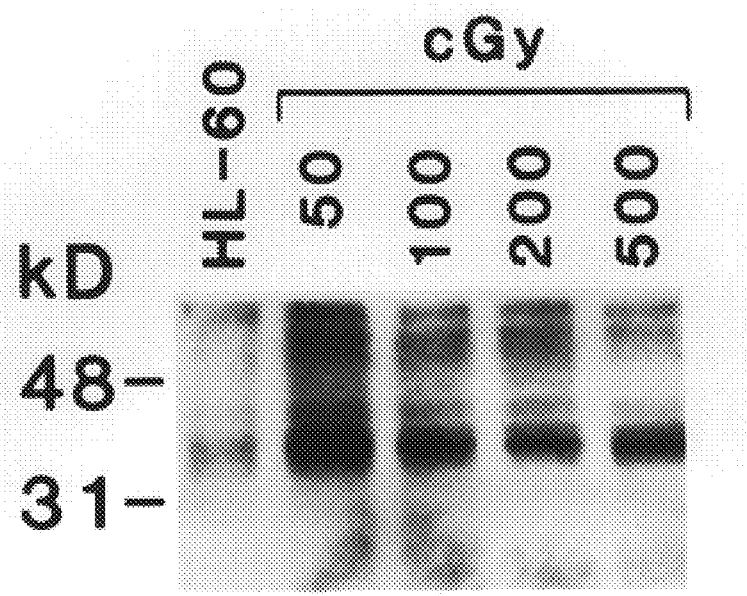
FIG. 14A and FIG. 14B. Different doses of ionizing radiation induce tyrosine phosphorylation of the 34 kD protein. HL-60 cells were exposed to the indicated doses of ionizing radiation and then harvested at 5 min.
Figure 14B:
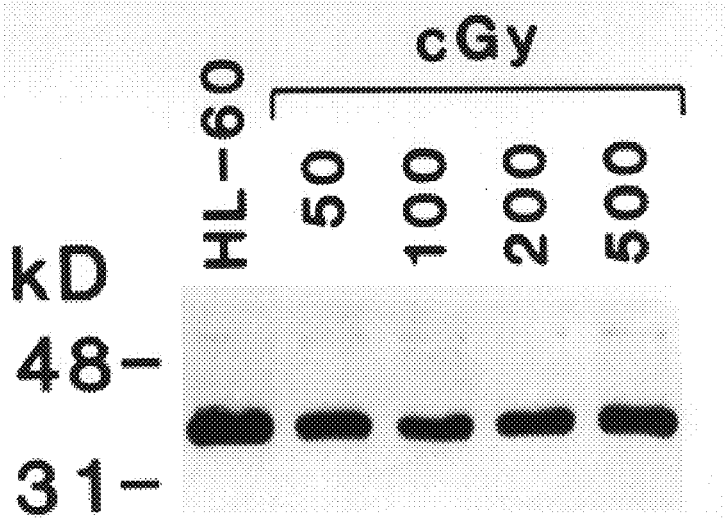

HL-60 cells were exposed to 200 cGy ionizing radiation and monitored for proteins with increased levels of phosphotyrosine. Using an anti-P-Tyr antibody in immunoblot analyses, reactivity with a protein of approximately 34 kD was increased at 1 min after ionizing radiation treatment (FIG. 13A). Similar findings were obtained at 5 and 10 min, while reactivity was decreased at 15 min (FIG. 13A). The filters were washed and reprobed with an anti-p34$^{cdc2}$ antibody. The anti-P-Tyr and anti-p34$^{cdc2}$ signals were superimposable. Moreover, there was little detectable change in p34$^{cdc2}$ protein levels following exposure to ionizing radiation (FIG. 13B). Similar findings were obtained with doses of ionizing radiation from 50 to 500 cGy (FIG. 14A). The finding that the signals obtained with the anti-p34$^{cdc2}$ antibody (FIG. 14B) were also superimposable over those found with anti-P-Tyr suggested that p34$^{cdc2}$ may undergo phosphorylation on tyrosine following ionizing radiation treatment.

Figure 15A:
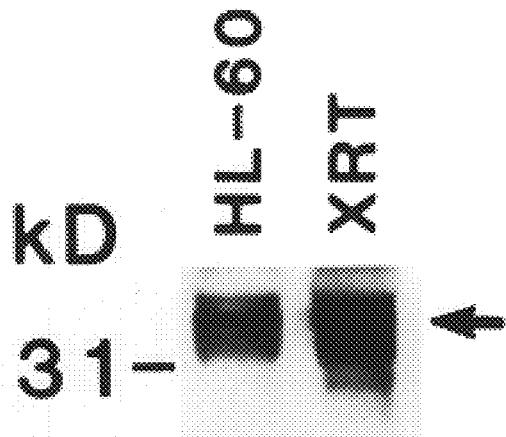
FIG. 15A and FIG. 15B. Ionizing radiation induces tyrosine phosphorylation of p34$^{cdc2}$. HL-60 cells were exposed to 50 cGy ionizing radiation and harvested at 5 min. Cell lysates from control and irradiated cells were subjected to immunoprecipitation (IP) with p34$^{cdc2}$ antiserum and protein A-Sepharose.
Figure 15B:
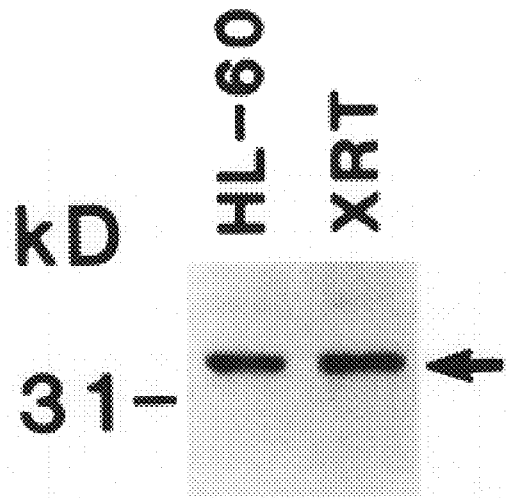

Extracts of irradiated cells were subjected to immunoprecipitation with anti-p34$^{cdc2}$. The immunoprecipitates were then monitored by immunoblotting with anti-P-Tyr. The signal for p34$^{cdc2}$ was increased in irradiated as compared to control cells (FIG. 15A). While this result further supported increased tyrosine phosphorylation of p34$^{cdc2}$ the filter was washed and reprobed with anti-p34$^{cdc2}$ to assay for levels of p34$^{cdc2}$ protein. The finding that the anti-p34$^{cdc2}$ signals were similar in control and irradiated cells (FIG. 15B) indicated that p34$^{cdc2}$ undergoes increased phosphorylation on tyrosine following ionizing radiation exposure.

Activation of p34$^{cdc2}$ requires association with cyclin B (Pines & Hunter, 1989; Russel & Nurse, 1987) and certain posttranslational modifications. In Schizosaccharomyces pombe, the p34$^{cdc2}$/cyclin B complex is inactivated by phosphorylation of p34$^{cdc2}$ on tyrosine 15 by Weel (Featherstone & Russell, 1991; Parker et al., 1991; 1992; Gould & Nurse, 1989). Dephosphorylation of p34$^{cdc2}$ on Tyr-15 by the cdc25 gene product is necessary for activation of p34$^{cdc2}$ and entry into mitosis (Gould et al., 1989; Enoch & Nurse, 1990). The weel and cdc25 gene products thus determine the timing of entry into mitosis by a series of phosphorylations and dephosphorylations of p34$^{cdc2}$. Other work in S. pombe has demonstrated that mitotic checkpoints monitor DNA synthesis and the presence of DNA damage (Al-Khodairy & Carr, 1992; Rowley et al., 1992; Lock & Ross, 1990). The DNA damage checkpoint evidently regulates p34$^{cdc2}$ by mechanisms distinct from those induced by the replication checkpoint (Rowley et al., 1992; Lock & Ross, 1990). Other studies have demonstrated that p34$^{cdc2}$ kinase activity is decreased when CHO cells are exposed to 8 Gy ionizing radiation (Uckun et al., 1992b).

The present invention discloses activation of Src-like tyrosine kinases and phosphorylation of tyrosine kinase substrates, such as p34$^{cdc2}$, as a rapid response to ionizing radiation. Inhibition of the radiation-induced activation of those tyrosine kinases prevents or inhibits substrate phosphorylation. Because the function of those substrates depends on their state of phosphorylation, inhibition of phosphorylation alters the function of those substrates. To the extent that substrate function is responsible for all or part of the cascade of changes associated with radiation, altering substrate function by inhibition of phosphorylation alters the cells response to radiation. Thus, the present invention contemplates a process to alter the response of cell to radiation, the process comprising inhibiting tyrosine kinase activity. In a preferred embodiment, the tyrosine kinase in a Src-like tyrosine kinase of the lyn family.

EXAMPLE III

DNA Damaging Agents

Following radiation exposure, many single strand breaks are produced in DNA, but these are readily repaired using the opposite strand of DNA as a template. X-ray energy deposition on DNA may lead not only to strand breakage but to base damage. The breakage may result in incorrect rejoining in pre-replication chromosomes in the $G_1$ phase, leading to chromosomal aberrations, or if the radiation is given late in S or $G_2$, chromatid aberrations will result.

The skilled artisan in directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

A variety of other DNA damaging agents may be used with the tyrosine kinase inhibitors, as provided by this invention. This includes agents that directly crosslink DNA, agents that intercalate into DNA, and agents that lead to chromosomal and mitotic aberrations by affecting nucleic acid synthesis.

Agents that induce DNA alkylation, such as mitomycin C, may be used. Mitomycin C is an extremely toxic antitumor antibiotic that is cell cycle phase-nonspecific. It is almost always given intravenously, at a dose of 20 mg/meter$^2$, either in a single dose or given in 10 separate doses of 2 mg/meter$^2$ each given over 12 days. It has been used clinically against a variety of adenocarcinomas (stomach, pancreas, colon, breast) as well as certain head and neck tumors.

Another option is to employ cisplatin, which has also been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis, and chromosomal segregation. Examples of these compounds include adriamycin, also known as doxorubicin, etoposide, verapamil, podophyllotoxin, and the like. Widely used in clinical setting for the treatment of neoplasms these compounds are administered through bolus injections intravenously at doses ranging from 25–75 mg/m2 at 21 day intervals for adriamycin, to 35–50 mg/m2 for etoposide, intravenously or double the intravenous dose orally.

Agents that disrupt the synthesis and fidelity of nucleic acid precursors, and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

EXAMPLE IV

Tyrosine Kinase Inhibitors

Tyrosine protein kinase activities are known to be associated with oncogene products of the retroviral src gene family, and also with several cellular growth factor receptors such as that for epidermal growth factor (EGF). Activation of protein tyrosine phosphorylation by p56/p53$^{lyn}$ in the present studies demonstrates that the lyn protein is associated with the cell cycle regulatory protein p34$^{cdc2}$, contributing to mitotic arrest. If this association is blocked, such as by use of protein tyrosine kinase inhibitors such as genistein or herbimycin A, the cells are unable to arrest in the G$_2$ phase, forcing cell cycle traverse and expression of potentially lethal damage. Thus, the combined use of DNA damaging agents such as ionizing radiation or alkylating agents with tyrosine kinase inhibitors is a novel approach to enhancing cell killing.

Genistein, a natural isoflavonoid phytoestrogen, has been reported to exhibit specific inhibitory activity against tyrosine kinases of EGF receptor, pp60$^{v-src}$ and pp110$^{gag-fes}$. It has been generally shown to block a number of EGF dependent phenomena, including both receptor autophosphorylation and histone phosphorylation.

Herbimycin A has also been shown to inhibit the autophosphorylation of EGF-stimulated receptors in intact cells in a time and dose dependent manner. Herbimycin A both decreases the receptor quantity and the EGF-stimulated receptor kinase activity.

Other tyrosine kinase inhibitors may also be used, for example, those isolated from natural sources. One such compound is erbstatin (Umezawa and Imoto M, 1991; Sugata et al., 1993) and its analogues, e.g., RG 14921 (Hsu et al., 1992). Lavendustin A from Streptomyces griseolavendus (Onoda et al., 1989), which is about 50 times more inhibitory than erbstatin, and analogues thereof, are also contemplated for use as protein-tyrosine kinase inhibitors (Smyth et al., 1993b). Piceatannol (3,4,3',5'-tetrahydroxy-trans-stilbene; Geahlen and McLaughlin, 1989) and polyhydroxylated stilbene analogues thereof (Thakkar et al., 1993) may also be used.

Further natural tyrosine kinase inhibitors that may be used are emodin (3-methyl-1,6,8-trihydroxyanthraquinone), an inhibitor from the Chinese medicinal plant Polygonum cuspidatum (Jayasuriya et al., 1992; Chan et al., 1993); desmal (8-formyl-2,5,7-trihydroxy-6-methylflavanone), isolated from the plant Desmos chinensis (Kakeya et al., 1993); the chlorosulfolipid, malhamensilpin A, isolated from the cultured chrysophyte Poterioochromonas malhamensis (Chen et al., 1994); flavonoids obtained from Koelreuteria henryi (Abou-Shoer et al., 1991); fetuin, a natural tyrosine kinase inhibitor of the insulin receptor (Rauth et al., 1992).

Another group of compounds known to be tyrosine kinase inhibitors are the tyrphostins, which are low molecular weight synthetic inhibitors (Gazit et al., 1989). The tyrphostins AG17, AG18, T23 and T47 have been shown to inhibit pancreatic cancer cell growth in vitro (Gillespie et al., 1993). Tyrphostins have also been shown to have antiproliferative effects on human squamous cell carcinoma in vitro and in vivo (Yoneda et al., 1991). RG-13022 and RG-14620 were found to suppress cancer cell proliferation in vitro and tumor growth in nude mice. Another active tyrphostin is AG879 (Ohmichi et al., 1993).

Various chemical compounds may also be used in combination with DNA damaging agents, such as ionizing radiation, as have been described in the literature for use alone. One example is RG50864 (Merkel et al., 1993). Further examples are the indole substituted 2,2'-dithiobis(l-methyl-N-phenyl-1H-indole-3-carboxamides, especially the 5-substituted derivative, as described by Rewcastle et al. (1994). (Z)-alpha-[(3,5-dichlorophenyl)methylene]-3-pyridylacetonitrile (RG 14620) is another active tyrosine kinase inhibitor that may be used in a topical or intravenous form (Khetarpal et al., 1994).

BE-23372M, (E)-3-(3,4-dihydroxybenzylidene)-5-(3,4-dihydroxyphenyl)-2(3H)-furanone, is also a tyrosine kinase inhibitor (Tanaka et al., 1994a). This may be synthesized from 3-(3,4-dimethoxybenzoyl)propionic acid and veratraldehyde or 3,4-diacetoxy-benzaldehyde, as described by Tanaka et al. (1994b). BE-23372M may also be isolated from the culture broth of a Rhizoctonia solani fungus (strain F23372) using acetone and then purified by solvent extraction and column chromatography (Okabe et al., 1994).

Further tyrosine kinase inhibitors that may be used include 4,5-Dianilinophthalimide, which has, alone, been shown to have in vivo antitumor activity (Buchdunger et al., 1994). Hydroxylated 2-(5'-salicyl)naphthalenes form another group of inhibitors that could be used in the present invention, and may be prepared as described by Smyth et al. (1993a).

EXAMPLE V

Treatment Protocols

1) Patients exhibiting neoplastic disease are treated with a protein kinase inhibitor, for example genistein, at a concentration of between 1 and 100 μM, or herbimycin A at a concentration of between about 1 and 100 μM, for 6 hours prior to exposure to a DNA damaging agent.
2) Patients are exposed to ionizing radiation (2 gy/day for up to 35 days), or an approximate a total dosage of 700 gy.

3) As an alternative to ionizing radiation exposure, patients are treated with a single intravenous dose of mitomycin C at a dose of 20 mg/m$^2$.

It is contemplated that mitomycin C treatment in combination with tyrosine protein kinase inhibitors will be effective against cancer of the stomach, pancreas, oral cavity, breast and head/neck.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abou-Shoer, M., Ma, GE., et al. (1993), *J Nat Prod*, 56(6):967–9.

Akiyama, T., Ishida, J., et al. (1987), *J. Biol. Chem.*, 262:5592–5595.

Al-Khodairy, F. and Carr, A. M. (1992), *EMBO J.*, 11:1343–1350.

Aruoma, O. I., Halliwell, B., et al. (1989), *Free Radicals Biol. Med.* 6:593–597.

Atherton-Fessler, S., Parker, L. L., et al. (1993), Mol. Cell. Biol., 13:1675–1685.

Barbet, N. C. and Carr, A. M. (1993), *Nature*, 364:824–827.

Barnekow, A. and Gessler, M. (1986), *EMBO J.*, 5:701–705.

Bhuyan, B. K., Smith, K. S., et al. (1992), *Cancer Res.*, 52:5687–5692.

Bonni, A., Frank, D. A., et al. (1993), *Science*, 262:1575–1579.

Brach, M. A., Hass, R., et al. (1991), *J. Clim. Invest.* 88:691–695.

Buchdunger, E., Trinks, U., (1994), *Proc Natl Acad Sci USA*, 91(6):2334–8.

Burgunder, J. M., Varriale, A., et al. (1989), *Eur. J. Clin. Pharmacol*, 36:127–131.

Cantley, L., Auger, K. R., et al. (1991), *Cell*, 64:281–302.

Carrano, A. V., Thompson, L. H., et al. (1979), *Mutat. Res.*, 63:175–178.

Carter, R. H., Park, D. J., et al. (1991), *Proc. Natl. Acad. Sci. USA*, 88:2745–2749.

Casillas, A., Hanekom, C., et al. (1991), *J. Biol. Chem.*, 266:19088–19094.

Chan, T. C., Chang, C. J., et al. (1993), *Biochem Biophys Res Commun*, 30(3):193.

Chen, J. L., Proteau, P. J., et al. (1994), *J Nat Prod*, 57(4):524–7.

Datta, R., Hallahan, D., et al. (1992b), *Biochemistry*, 31:8300–8306.

Datta, R., Rubin, E., et al. (1992a), *Proc. Natl. Acad. Sci. USA*, 89:10149–10153.

Datta, R., Taneja, N., et al. (1993), *Proc. Natl. Acad. Sci. USA*, 90:2419–2422.

Desai, D., Gu, Y. et al. (1992), *Mol. Biol. Cell*, 3:571–582.

Devary, Y., Gottlieb, R. A., et al. (1992), *Cell*, 71:1081–1091.

dGold, M. R., Chan, V. W.-F., et al. (1992b), *J. Immunol*, 148:2012–2017.

Dusre, L., Covey, J. M., et al. (1989), *Chem.-Biol. Interactions*, 71:63–78.

Enoch, T. and Nurse, P. (1990), *Cell*, 60:665–673.

Ewig, R. A. and Khon, K. W. (1977), *Cancer Res.*, 37:2114–2122.

Featherstone, C. and Russell, P. (1991), *Nature*, 349:808–811.

Gazit, A., Yaish, P., et al. (1989), *J Med Chem*, 32(10):2344–52.

Geahlen, R. L. and McLaughlin, J. L. (1989), *Biochem Biophys Res Commun*, 165(1):241–5.

Gee, C. E., Griffin, J., et al. (1986), *Proc. Natl. Acad. Sci. USA*, 83:5131–5135.

Gillespie, J., Dye, J. F., et al. (1993), *Br J Cancer*, 68(6):1122–6.

Gold, M. R., Crowley, M. T., et al. (1992a), *J. Immunol.*, 148:2012–2022.

Gould, K. and Nurse, P. (1989), *Nature*, 342:39–44.

Gould, K. L., Moreno, S., et al. (1990), *Science*, 250:1573–1576.

Hall, E. J. (1988), In: *Radiobiology for the Radiologist*, 3rd Edition, ed. Hall, E. J. (Lippincott, Philadelphia), pp. 17–38.

Hallahan, D., Sukhatme, V., et al. (1991), *Proc. Natl. Acad. Sci. USA* 88:2156–2160.

Hanks, S. J., Quinn, A. M. et al. (1988), *Science*, 241:42–52.

Hartley, J. A., Bingham, J. P. et al. (1992), *Nucleic Acids Res.*, 20:3175–3178.

Hartwell, L. H. and Weinert, T. A. *Science*, 246:629–634, 1989.

Hempel, W. M., Schatzman, R. C. et al. (1992), *J. Immunol.*, 148:3021–3025.

Hidaka, H., Inagaki, M., et al. (1984), *Biochemistry*, 23:5036–5041.

Hsu, C. Y., Jacoski, M. V., et al. (1992), *Biochem Pharmacol*, 43(11):2471–7.

Hurley, L. H., Reynolds, V. L., et al. (1984), *Science*, 226:843–844.

Jayasuriya, H., Koonchanok, N. M., et al. (1992), *J Nat Prod*, 55(5):696–8.

Kakeya, H., Imoto, M., et al. (1993), *FEBS Lett*, 320(2): 169–72.

Kastan, M. B., Zhan, Q., et al. (1992), *Cell*, 71:587–597.

Kastan, M., Onyekware, O., et al. (1991), *Cancer Res.*, 51:6304–6311.

Katagiri, K., Katagiri, T., et al. (1991), *J. Immunol.*, 146:701–707.

Khetarpal, V. K., Markham, P. M., et al. (1994), *Drug Metab Dispos*, 22(2):216–23.

Konopa, J. (1988). *Biochem. Pharmacol.*, 37:2303–2309.

Larner, A. C., David, M., et al. (1993), *Science*, 261:1730–1733.

Lau, C. C. and Pardee, A. B. (1982), *Proc. Natl. Acad. Sci. USA*, 79:2942–2946.

Lock, R. B. and Ross, W. E. (1990), *Cancer Res.*, 50:3761–3766.

Merkel, L. A., Rivera, L. M., et al. (1993), *Biochem Biophys Res Commun*, 192(3):1319–26.

Murray, A. (1989), *Nature*, 341:14–15.

Mustalin, T., and Altman, A. (1990), *Oncogene* 5:809–813.

Nakamura, K., Hori, T., et al. (1993), *Oncogene S*, 3133–3139.

Nakamura, S., Yanagi, S., et al. (1988), *Eur. J. Biochem.*, 174:471–477.

Norbury, C., and Nurse, P. (1992), *Ann. Rev. Biochem.*, 61:441–470.

Nurse, P. (1990), *Nature*, 344:503–507.

O'Connor, P. M., Ferris, D. K., et al. (1992), *Cell Growth & Differ.*, 3:43–52.

Ohmichi, M., Pang, L., et al. (1993), *Biochemistry*, 32(17): 4650–8.

Okabe, T., Yoshida, E., et al. (Mar 1994), *J Antibiot*, 47(3):289–93.

Onoda, T., Iinuma, H., et al. (1989), *J Nat Prod*, 52(6):1252–7.

Parker, L. L., Atherton-Fessler, S., et al. (1991), *EMBO J.*, 10:1255–1263.

Parker, L. L., Atherton-Fessler, S., et al. (1992), *Proc. Natl. Acad. Sci. USA*, 89:2917–2921.

Parker, L. L., Atherton-Fessler, S., et al. (1991), *EMBO J.*, 10:1255–1263.

Pines, J. and Hunter, T. (1990), *New Biol.*, 2:389–401.

Pines, J., and Hunter, T. (1989), *Cell*, 58:833–846.

Pleiman, C. M., Clark, M. R., et al. (1993), *Mol. Cell. Biol.*, 13:5877–5887.

Rauth, G., Poschke, O., et al. (1992), *Eur J Biochem*, 204(2):523–9.

Rewcastle, G. W., Palmer, B. D., et al. (1994), *J Med Chem*, 37(13):2033–42.

Roederer, M., Staal, F. J. T., et al. (1990), *Proc. Natl. Acad. Sci. USA*, 87:4884–4888.

Rowley, R., Subramani, S., et al. (1992), *EMBO J.*, 11:1335–1342.

Ruff-Jamison, S. R., Chen, K. et al. (1993), *Science*, 261, 1733–1736.

Russell, P., and Nurse, P. (1987), *Cell*, 45:559–567.

Schiestl, R. H., Reynolds, P., et al. (1989), *Mol. Cell. Biol.*, 9:182–1896.

Sherman, M., Stone, R., et al. (1990) *J. Biol. Chem.*, 265:3320–3323.

Sherman, S. E. and Lippard, S. J. (1987), *Chem. Rev.*, 87:1153–1181.

Smyth, M. S., Stefanova, I., et al. (1993b), *J Med Chem*, 36(20):3010–4.

Smyth, M. S., Stefanova, I., et al. (1993a), *J Med Chem*, 36(20):3015–20.

Solomon, M. J., Lee, T. et al. (1992)., *Mol. Biol. Cell*, 3:13–27.

Staal, F. J. T., Roederer, M., et al. (1990), *Proc. Natl. Acad. Sci. USA*, 87:9943–9947.

Stein, B., Rahmsdorf, H. J., et al. (1989), *Mol. Cell. Biol.*, 9:5169–5181.

Steinmann, K. E., Belinsky, G. S., et al. (1991), *Proc. Natl. Acad. Sci. USA*, 88:6843–6847.

Sugata, D., Yamashita, K., et al. (1993), *Biochem Biophys Res Commun*, 194(1)

Tanaka, S., Okabe, T., et al. (1994b), *Antibiot (Tokyo)*, 47(3):297–300.

Tanaka, S., Okabe, T., et al. (1994a), *J Antibiot (Tokyo)*, 47(3):294–6.

Thakkar, K., Geahlen, R. L., et al. (1993), *J Med Chem*, 36(20):2950–5.

Tobey, R. A. (1975), *Nature*, 254:245–247.

Tomasz, M., Chawla, A. K., et al. (1988), *Biochemistry*, 27:3182–3187.

Uckun, F. M., Schievan, G. L., et al. (1993), *Proc. Natl. Acad. Sci. USA*, 90:252–256.

Uckun, F. M., Tuel-Ahlgren, L., et al. (1992a), *Proc. Natl. Acad. Sci. USA*, 89:9005–9009.

Uehara, Y., Murakami, Y., et al. (1989), *Cancer Res.*, 49:780–785.

Umezawa, K. and Imoto, M. (1991), *Methods Enzymol*, 201:379–85.

Weinert, T. and Hartwell, L. (1988), *Science*, 241:317–322.

Wong, T. W. and Goldberg, A. R. (1984), *J. Biol. Chem.*, 259:8505–8512.

Yamanashi, Y., Fukui, Y., et al. (1992), *Proc. Natl. Acad. Sci. USA*, 89:1118–1122.

Yamanashi, Y., Fukushige, S., et al. (1987), *Mol. Cell. Biol.*, 7:237–243.

Yamanashi, Y., Mori, S., et al. (1989), *Proc. Natl. Acad. Sci. USA*, 86:6538–6542.

Yoneda, T., Lyall, R. M., et al. (1991), *Cancer Res*, 51(16):4430–5.

Zioncheck, T. F., Harrison, M. L. et al. (1986), *J. Biol. Chem.*, 261:15637–15643.

What is claimed is:

1. A process of increasing cell death comprising the steps of:
   (a) treating cells with a DNA damaging agent; and
   (b) contacting the cells with a protein tyrosine kinase inhibitor.

2. The process of claim 1, wherein the protein tyrosine kinase inhibitor is genistein or herbimycin A.

3. The process of claim 1, wherein the DNA damaging agent is ionizing radiation.

4. A method for the treatment of neoplastic disease in a patient comprising the steps of:
   (a) administering to the patient a pharmaceutically acceptable preparation which includes a therapeutically effective amount of a tyrosine kinase inhibitor; and
   (b) treating neoplastic cells with a therapeutically effective amount of a DNA damaging agent.

5. The method of claim 4, wherein the tyrosine kinase inhibitor is genistein or herbimycin A.

6. The method of claim 4, wherein the DNA damaging agent is ionizing radiation or an alkylating agent.

7. A method of increasing the effect of ionizing radiation on cell killing, comprising the steps of:
   (a) treating the cells with a therapeutically effective amount of ionizing radiation; and
   (b) contacting the cells with a protein tyrosine kinase inhibitor.

8. The process of claim 7, wherein the protein kinase inhibitor is genistein or herbimycin A.

9. The process according to claim 8, wherein the protein tyrosine kinase inhibitor is herbimycin A.

* * * * *

UNITED STATES PATENT AND TRADEMARK OFFICE
CERTIFICATE OF CORRECTION

PATENT NO. : 6,524,832 B1
DATED : February 25, 2003
INVENTOR(S) : Kufe et al.

It is certified that error appears in the above-identified patent and that said Letters Patent is hereby corrected as shown below:

Column 26,
Line 33, please delete "or an alkylating agent" therefor.
Line 41, please delete "process" and insert -- method -- therefor.
Line 43, please delete "process" and insert -- method -- therefor.

Signed and Sealed this

Twenty-fifth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,524,832 B1  Page 1 of 1
APPLICATION NO. : 08/309315
DATED : February 25, 2003
INVENTOR(S) : Donald Kufe and Ralph R. Weichselbaum It is certified that error appears in the above-identified patent and that said Letters Patent is hereby corrected as shown below:

Title page at (22), please delete "Aug. 19, 1994" and insert --Sep. 19, 1994-- therefor.

Signed and Sealed this

Twenty-sixth Day of August, 2008

JON W. DUDAS
*Director of the United States Patent and Trademark Office*